(12) United States Patent
Deshaies et al.

(10) Patent No.: US 10,005,735 B2
(45) Date of Patent: Jun. 26, 2018

(54) INHIBITORS OF RPN11

(71) Applicant: California Institute of Technology, Pasadena, CA (US)

(72) Inventors: Raymond J. Deshaies, Pasadena, CA (US); Jing Li, Arcadia, CA (US); Seth Cohen, San Marcos, CA (US); Christian Perez, La Jolla, CA (US); Yuyong Ma, San Diego, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/239,795

(22) Filed: Aug. 17, 2016

(65) Prior Publication Data

US 2017/0050931 A1    Feb. 23, 2017

Related U.S. Application Data

(60) Provisional application No. 62/206,034, filed on Aug. 17, 2015.

(51) Int. Cl.
| | |
|---|---|
| *C07D 215/54* | (2006.01) |
| *C07D 413/12* | (2006.01) |
| *C07D 417/12* | (2006.01) |
| *C07D 405/12* | (2006.01) |
| *C07D 409/12* | (2006.01) |
| *C07D 401/12* | (2006.01) |

(52) U.S. Cl.
CPC ......... *C07D 215/54* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
CPC .. C07D 215/54; C07D 413/12; C07D 417/12; C07D 405/12; C07D 409/12; C07D 401/12
See application file for complete search history.

(56) References Cited

U.S. PATENT DOCUMENTS

2014/0235548 A1   8/2014 Zhou et al.

FOREIGN PATENT DOCUMENTS

WO    WO 2012/158435    * 11/2012    ............. C12N 5/07

OTHER PUBLICATIONS

STN compound data (Year: 2017).*
National Center for Biotechnology Information. PubChem BioAssay Database; AID=588493, https://pubchem.ncbi.nlm.nih.gov/bioassay/588493, Oct. 12, 2011, 14pp.
National Center for Biotechnology Information. PubChem BioAssay Database; AID=651999, https://pubchem.ncbi.nlm.nih.gov/bioassay/651999. Jan. 30, 2013, 14pp.
Arnst, Jamie et al.; "High-throughput compatible FRET based assay to identify small molecule inhibitors of AMSH deubiquitinase activity," Anal Biochem; Sep. 1, 2013; 440(1); pp. 71-77.
Chou, Tsui-Fen et al.; "Quantitative Cell-based Protein Degradation Assays to Identify and Classify Drugs That Target the Ubiquitin-Proteasome System," J. Biol. Chem.; May 13, 2011; 286(19); pp. 16546-16554.
International Search Report and Written Opinion dated Dec. 30, 2016 for corresponding International Application No. PCT/US2016/047439, 9pp.

* cited by examiner

*Primary Examiner* — Angela C Brown-Pettigrew
(74) *Attorney, Agent, or Firm* — Lewis Roca Rothgerber Christie LLP

(57) ABSTRACT

Candidate compounds for specific inhibition of Rpn11 are represented by Formula 1a

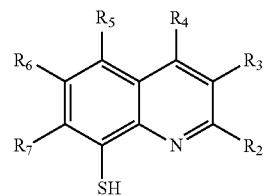

Formula 1a where each of $R_2$, $R_3$, $R_4$, $R_5$, $R_6$, and $R_7$ is independently selected from hydrogen (H), substituted and unsubstituted alkyl groups, carboxyl groups, or substituted and unsubstituted carboxyamides.

18 Claims, No Drawings

INHIBITORS OF RPN11

CROSS-REFERENCE TO RELATED APPLICATION(S)

The present application claims priority to and the benefit of U.S. Provisional Application Ser. No. 62/206,034 filed on Aug. 17, 2015, entitled "Novel Proteasome Inhibitors Targeting Essential Deubiquitinase Subunit Rpn11," the entire content of which is incorporated herein by reference.

STATEMENT REGARDING FEDERALLY SPONSORED RESEARCH OR DEVELOPMENT

This invention was made with government support under Grant No. CA164803 awarded by the National Institutes of Health. The government has certain rights in the invention.

BACKGROUND

Multiple myeloma (MM) is a plasma cell neoplasm that affects thousands of people each year. Currently, there is no cure for MM, few if any patients survive, and even with a strong regimen of conventional chemotherapy and radiation, life expectancy is on average three years. The recent development of novel chemotherapeutics that inhibit components of the proteasome have proven very successful in extending progression-free and overall survival. These drugs inhibit the ubiquitin-proteasome degradation pathway through binding to one or more of the protease active sites within the proteasome.

The ubiquitin-proteasome system (UPS) plays an essential role in protein quality control by degrading unwanted or misfolded proteins within cells. The UPS helps maintain cell homeostasis and regulates numerous processes including cell cycle, apoptosis, transcription, and DNA repair. Inhibition of the UPS induces apoptosis by preventing degradation of pro-apoptotic proteins, thereby facilitating activation of programmed cell death. Inhibiting the UPS pathway was validated as a clinical target with the FDA approval of bortezomib (marketed as Velcade, Millennium Pharmaceuticals), followed by carfilzomib (marketed as Kyprolis, Onyx Pharmaceuticals), and most recently ixazomib (marketed as Ninlaro, Takeda Pharmaceuticals), all approved for treatment of MM.

Protein degradation through the proteasome (i.e., proteolysis) occurs through a long complex pathway. Proteolysis is initiated through ATP-dependent activation of ubiquitin by E1 proteins. Through a series of steps involving E2 and E3 proteins, the protein destined for degradation becomes tagged with ubiquitin. The ubiquitin-tagged protein undergoes several rounds of ubiquitin ligation resulting in polyubiquitination. The 19S regulatory system of the proteasome recognizes polyubiquitination, and then traps and unfolds the polyubiquitinated protein, which is then translocated into the active site of the 20S complex, and expelled as oligopeptides. It is the proteasome regulatory particle lid subunit (Rpn11) zinc(II) ($Zn^{2+}$) metallo-isopeptidase subunit within the 19S complex that hydrolyzes the polyubiquitin bound to the protein and releases the ubiquitin into the cytoplasm to be recycled. This crucial ubiquitin recycling step catalyzed by Rpn11 is necessary for protein degradation to occur, and inhibition of this crucial step is a target for proteasome inhibition and cell apoptosis.

SUMMARY

Embodiments of the present invention include compounds represented by Formula 1a

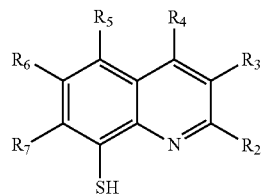

Formula 1a where each of $R_2$, $R_3$, $R_4$, $R_5$, $R_8$, and $R_7$ is independently selected from hydrogen (H), substituted and unsubstituted alkyl groups, carboxyl groups, or substituted and unsubstituted carboxyamides.

In some embodiments of the present invention, a compound is represented by Formula 1a where each of $R_2$, $R_3$, $R_4$, $R_5$, $R_8$, and $R_7$ is independently selected from H, substituted and unsubstituted C1-C12 alkyl groups, carboxyl groups, or substituted and unsubstituted carboxyamides. In some embodiments, a compound is represented by Formula 1a where substituted alkyl groups are selected from amines, amides, carboxy groups, carboxyl groups, or thiols.

In some embodiments of the present invention, a compound is represented by Formula 1a where at least one of $R_2$, $R_3$, $R_4$, $R_5$, $R_8$, and/or $R_7$ of Formula 1a is a group represented by Formula 1b

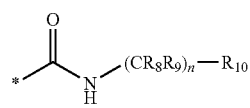

Formula 1b where n is 0, 1, 2, 3, or 4; * represents a binding site to Formula 1a; each of $R_8$ and $R_9$ are independently selected from hydrogen or unsubstituted alkyl groups; and $R_{10}$ is selected from H, acetate, methyl acetate, CH2(CO)OCH3, oxazole, thiazole, tetrahydrofuran, furan, thiophene, pyridine, benzene, fluorobenzene, trifluorobenzene, methoxybenzene, dioxolylmethylbenzene, morphilino, or morpholinobenzene.

In some embodiments of the present invention, a compound is represented by Formula 1a where at least one of $R_2$, $R_3$, $R_4$, $R_5$, $R_6$, and/or $R_7$ of Formula 1a is a group represented by Formula 1b and where $R_{10}$ is selected from a group represented by Formulae 2 through 5.

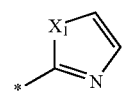

Formula 2

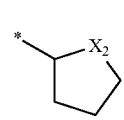

Formula 3

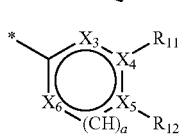

Formula 4 where each of $X_1$, $X_2$, $X_3$, $X_4$, $X_5$, and $X_6$ is independently selected from S, C, N, or O; $R_{11}$ and $R_{12}$ are each independently selected from H, substituted or unsubstituted alkyl groups, fluorine (F), trifluoromethyl, carboxyl groups, CO2CH2CH3, OCH3, benzene, or morpholino, and a is 0 or 1, and when a is 1, $X_5$ and $X_6$ form a pi bond.

In some embodiments of the present invention, a compound is represented by Formula 1a where at least one of $R_2$, $R_3$, $R_4$, $R_5$, $R_6$, and/or $R_7$ of Formula 1a is a group represented by Formula 1b and where $R_{10}$ is represented by Formula 2a

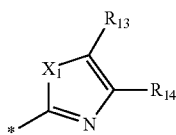

Formula 2a where $X_1$ is S, C, N, or O; and $R_{13}$ and $R_{14}$ are each independently selected from from H, substituted or unsubstituted alkyl groups, fluorine (F), trifluoromethyl, carboxyl groups, CO2CH2CH3, OCH3, benzene, or morpholino.

In some embodiments of the present invention, a compound of Formula 1a is selected from one of Compounds 1-32.

In some embodiments of the present invention, a compound that specifically inhibits Rpn11 is represented by Formula 1a as disclosed herein.

In some embodiments of the present invention, a method of inhibiting Rpn11 in a cell, a cell culture, or a cell in a human or animal subject, includes administering a compound represented by Formula 1a as disclosed herein to the cell, the cell culture, or to the cell in a human or animal subject.

DETAILED DESCRIPTION

Embodiments of the present invention include candidate metal binding pharmacophore (MPB) compounds useful in identifying inhibitors of proteasome degradation through inhibition of the deubiquitinating isopeptidase enzyme Rpn11, and their synthesis and characterization.

Candidate compounds according to embodiments of the present invention were synthesized as described herein. Candidate compounds were screened for Rpn11 inhibition using an in vitro biochemical assay as previously described in PubChem AID 588493, SBCCG-A706-Rpn11-Inh-Primary-Assay, Oct. 12, 2011, the entire content of which is herein incorporated. In brief, this Rpn11 bioassay employs a fluorescent polarization readout based on the ability of the 26S proteasome to cleave the protein substrate including four tandem ubiquitin proteins fused to a peptide having a unique cysteine labeled with a fluorophore. Cleavage of this substrate by Rpn11 at the junction between the fourth ubiquitin and the peptide, releases the low molecular weight fluorescent peptide. Accordingly, inhibition of fluorescence correlates with inhibition of Rpn11. Inhibition is reported as the half maximal inhibitory concentration ($IC_{50}$) for the candidate compound.

The catalytic JAB1/MPN/Mov34 metalloenzyme (JAMM) motif of Rpn11 is found in 7 different human proteins including the Csn5 subunit of the COP9 signalosome, AMSH, AMSH-LP, the BRCC36 subunit of BRISC, MPND, and MYSM1. All of these enzymes cleave the isopeptide linkage that joins ubiquitin (or the ubiquitin-like protein Nedd8 in the case of Csn5) to a second molecule of ubiquitin or to a substrate. The conserved JAMM domain has the consensus sequence EXnHS/THX7SXXD, in which the histidine (His) and aspartic acid (Asp) residues bind the $Zn^{2+}$ ion and the fourth coordination site is occupied by a water molecule that is engaged in hydrogen bonding with a conserved glutamic acid (Glu). The $Zn^{2+}$ acts as a Lewis acid and increases the nucleophilic character of the bound water enough to allow hydrolytic cleavage of the isopeptide bond.

The candidate Rpn11 inhibiting compounds according to embodiments of the present invention were developed from an original screening of a metal binding pharmacophores (MBPs) library as described in Zhou et al., US 2014/0235548, "Compositions and Methods for JAMM Protein Inhibition," the entire content of which is herein incorporated by reference. Screening of this MPB library using the Rpn11 assay yielded a highly potent fragment, 8-thioquinoline (8TQ) as shown in Table 1 in comparison with other MPB compounds.

TABLE 1

| Structure | Rpn11 $IC_{50}$ (μM) | Structure | Rpn11 $IC_{50}$ (μM) |
|---|---|---|---|
| 8TQ (quinoline-SH) | 2.8 ± 0.35 | quinoline-NH2 | >100 |
| naphthalene-SH | >100 | quinoline-S-methyl | >100 |
| methyl-quinoline | >100 | quinoline-SH | >100 |
| quinoline-OH | >100 | 8e (naphthyridine-SH) | 15 |

Further development of derivatives based on potent inhibitors of the Rpn11 screening assay led to candidate compounds including the 8-thioquinoline (8TQ) structure.

In some embodiments of the present invention, compounds were identified and synthesized that specifically inhibit Rpn11 and do not inhibit (e.g., do not inhibit with the same potency, exhibit reduced inhibition compared to Rpn11, or do not inhibit) other JAMM domain enzymes that participate in proteasome degradation. To identify these Rpn11 specific inhibitors, candidate compounds were also assayed in a CP9/signalsome subunit 5 (Csn5) assay and an associated molecule with the SH3 domain of STAM (AMSH) assay as described respectively in PubChem AID 651999, SBCCG-A954-CSN5-Inh-Primary-Assay, Jan. 30, 2013, and Arnst et al., 2013, "High-throughput compatible fluorescence resonance energy transfer-based assay to identify small molecule inhibitors of AMSH deubiquitinase activity," *Anal Biochem*, 440; 71-77, the entire contents of both of which are herein incorporated by reference.

In other embodiments of the present invention, compounds were identified that inhibit Rpn11 as well as Csn5 and/or AMSH.

In addition to the Rpn11, Csn5, and AMSH enzymatic cell-free assays, candidate compounds were assayed in a reporter degradation assay to characterize the compound activity in cellulo in Hela cells as described in Chou and Deshaies, 2011, "Quantitative Cell-based Protein Degradation Assays to Identify and Classify Drugs That Target the Ubiquitin-Proteasome System," *JBC*, 286:16546-16554, the entire content of which is herein incorporated by reference.

According to embodiments of the present invention, inhibitors of Rpn11 include compounds having an 8TQ structure that inhibit Rpn11 in the Rpn11 assay with an $IC_{50}$ of 10 μm or less, 9 μm or less, 8 μm or less, 7 μm or less, 6 μm or less, 5 μm or less, 4 μm or less, 3 μm or less, 2 μm or less, or 1 μm or less.

According to embodiments of the present invention, specific inhibitors of Rpn11 include compounds having an 8TQ structure that inhibit fluorescence in the Rpn11 assay with an $IC_{50}$ of 1 μm or less, but that inhibit Csn5 and/or AMSH with an $IC_{50}$ of above 1 μm. This discrepancy in inhibition between Rpn11 and Csn5 and/or AMSH indicates specificity of the compounds for inhibition of Rpn11.

According to embodiments of the present invention, inhibitors of Rpn11 that are capable of in cellulo proteasome inhibition include compounds having an 8TQ structure that inhibit Rpn11 and proteasome protein degradation in the respective in vitro Rpn11 and proteasome assays disclosed herein. In some embodiments, for example, inhibitors of Rpn11 include compounds having an 8TQ structure that inhibit Rpn11 with an $IC_{50}$ of 3 μm or less and that inhibit in cellulo proteasome protein degradation with an $IC_{50}$ of 10 μm or less (for example, 9 μm or less, 8 μm or less, 7 μm or less, 6 μm or less, 5 μm or less, 4 μm or less, 3 μm or less, 2 μm or less, or 1 μm or less). In some embodiments of the present invention, inhibitors of Rpn11 that are capable of in cellulo proteasome inhibition include compounds having an 8TQ structure that inhibit Rpn11 with an $IC_{50}$ of 1 μm or less, and that inhibit protein degradation with an $IC_{50}$ of 1 μm or less. In some embodiments, for example, specific inhibitors of Rpn 11 that are capable of in cellulo proteasome inhibition include compounds having an 8TQ structure that inhibit Rpn11 with an $IC_{50}$ of less than 1 μm, that inhibit proteasome degradation with an $IC_{50}$ of less than 1 μm, and that inhibit Csn5 and/or AMSH with an $IC_{50}$ greater than 1 μm, greater than 2 μm, or greater than 3 μm (or that do not inhibit Csn5 and/or AMSH).

In some embodiments of the present invention, suitable compounds having an 8TQ structure include those represented by Formula 1a, below.

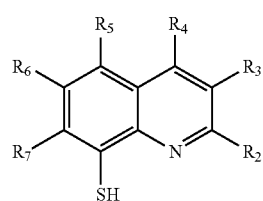

Formula 1a

In Formula 1a, each of $R_2$, $R_3$, $R_4$, $R_5$, $R_6$, and $R_7$ is independently selected from hydrogen (H), substituted and unsubstituted alkyl groups, carboxyl groups, or substituted and unsubstituted carboxyamides. In some embodiments, for example, each of $R_2$, $R_3$, $R_4$, $R_5$, $R_6$, and $R_7$ is independently selected from H, substituted and unsubstituted C1-C12 alkyl groups, carboxyl groups, and substituted and unsubstituted carboxyamides, for which the substituted alkyl groups include amines, amides, carboxy groups, carboxyl groups, and/or thiols. In some embodiments for example, the substituted carboxyamides include substituted and unsubstituted C1-C12 alkyl groups, acetate, oxazole, thiazole, tetrahydrofuran, furan, thiophene, pyridine, benzene, fluorobenzene, trifluorobenzene, methoxybenzene, dioxolylmethylbenzene, morphilino, and/or morpholinobenzene. In some embodiments, the substituted C1-C12 alkyl groups on the carboxyamides include acetate, oxazole, thiazole, tetrahydrofuran, furan, thiophene, pyridine, benzene, fluorobenzene, trifluorobenzene, methoxybenzene, dioxolylmethylbenzene, morphilino, and/or morpholinobenzene In some embodiments, at least one of $R_2$, $R_3$, $R_4$, $R_5$, $R_6$, and/or $R_7$ of Formula 1a is a group represented by Formula 1b, below.

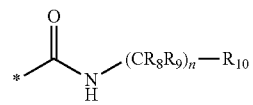

Formula 1b

In Formula 1b, n is 0, 1, 2, 3, or 4, and * represents a binding site to the 8TQ structure. Additionally, each of $R_8$ and $R_9$ are independently selected from hydrogen or unsubstituted alkyl groups.

Also, $R_{10}$ in Formula 1b may be selected from H, acetate, methyl acetate, CH2(CO)OCH3, oxazole, thiazole, tetrahydrofuran, furan, thiophene, pyridine, benzene, fluorobenzene, trifluorobenzene, methoxybenzene, dioxolylmethylbenzene, morpholino, or morpholinobenzene. In some embodiments, for example, $R_{10}$ in Formula 1b may be selected from groups represented by Formulae 2 through 5.

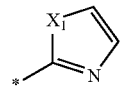

Formula 2

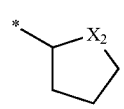

Formula 3

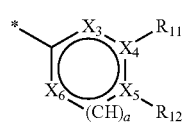

Formula 4

In Formulae 2 through 5, each of $X_1$, $X_2$, $X_3$, $X_4$, $X_5$, and $X_6$ is independently selected from S, C, N, or O. Also, $R_{11}$ and $R_{12}$ are each independently selected from H, substituted or unsubstituted alkyl groups, fluorine (F), trifluoromethyl, carboxyl groups, CO2CH2CH3, OCH3, benzene, and/or morpholino. In some embodiments, $R_{11}$ and $R_{12}$ are each independently selected from H, substituted or unsubstituted C1-C12 alkyl groups, fluorine (F), trifluoromethyl, carboxyl groups, CO2CH2CH3, OCH3, benzene, and/or morpholino. In some embodiments, the substituted alkyl groups include amines, amides, carboxy groups, carboxyl groups, and/or thiols. In some embodiments, $R_{11}$ and $R_{12}$ are each independently selected from H, substituted or unsubstituted C1-C4 alkyl groups, fluorine (F), trifluoromethyl, carboxyl groups, CO2CH2CH3, OCH3, benzene, and/or morpholino. Additionally, a is 0 or 1, and when a is 1, $X_5$ and $X_6$ form a pi bond.

In some embodiments, $R_{10}$ in Formula 1b may be selected from one of Formula 5 and 6.

Formula 5

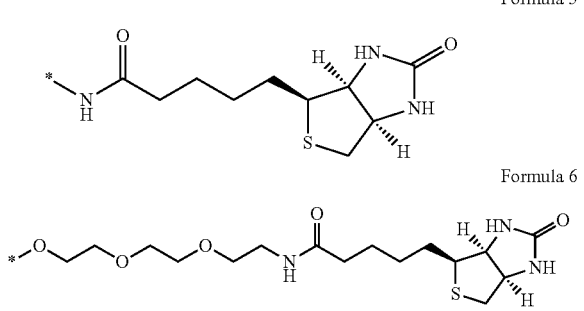

Formula 6

Synthetic protocols and reaction schemes for compounds of Formulae 1a, 1b and 2-6 are disclosed in Examples 2-74, of this disclosure.

In some embodiments, suitable compounds having an 8TQ structure include those represented by Formula 1a where at least one of $R_2$, $R_3$, $R_4$, $R_5$, $R_6$, and/or $R_7$ is represented by Formula 1b, and $R_{10}$ of Formula 1b is represented by Formula 4. In some embodiments, suitable compounds having an 8TQ structure include those represented by Formula 1a where at least one of $R_3$, $R_4$, $R_5$, and/or $R_6$ is represented by Formula 1b, each of $R_2$ and $R_7$ are hydrogen (H), and $R_{10}$ of Formula 1b is represented by Formula 4. In some embodiments, suitable compounds having an 8TQ structure include those represented by Formula 1a where one of $R_3$, $R_4$, $R_5$, and/or $R_6$ is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 4.

In some embodiments, suitable compounds having an 8TQ structure include derivatives of Compound 12 (Table 2) which are represented by a compound of Formula 1a where at least one of $R_2$, $R_3$, $R_4$, $R_5$, $R_6$, and/or $R_7$ is represented by Formula 1b, and $R_{10}$ of Formula 1b is represented by Formula 2a (a derivative of Formula 2) as shown below. Any variable not specified for Formula 1a, 1b, or 2 is as defined herein for each respective formula. Any variable not specified for Formula 2a is as defined in Formula 2.

Formula 2a

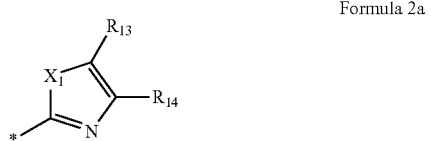

In Formula 2a, $X_1$ is S, C, N, or O and $R_{13}$ and $R_{14}$ are each independently selected from from H, substituted or unsubstituted alkyl groups, fluorine (F), trifluoromethyl, carboxyl groups, CO2CH2CH3, OCH3, benzene, and/or morpholino. In some embodiments, substituents of the substituted alkyl groups include amines, amides, carboxy groups, carboxyl groups, and/or thiols.

In some embodiments of the present invention, suitable compounds having an 8TQ structure include derivatives of Compound 12 represented by Formula 1a where at least one of $R_3$, $R_4$, $R_5$, and/or $R_6$, is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure include derivatives of Compound 12 represented by Formula 1a where one of $R_3$, $R_4$, $R_5$, and/or $R_6$, is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 2a.

In some embodiments of the present invention, suitable compounds having an 8TQ structure include derivatives of Compound 12 represented by Formula 1a where at least one of $R_3$ or $R_4$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure include derivatives of Compound 12 represented by Formula 1a where one of $R_3$ or $R_4$ is represented by Formula 1b, the one of $R_3$ or $R_4$ that is not represented by Formula 1b is hydrogen, each of $R_2$, $R_5$, $R_6$, and $R_7$ are hydrogen (H), and $R_{10}$ of Formula 1b is represented by Formula 2a.

In some embodiments of the present invention, suitable compounds having an 8TQ structure include derivatives of Compound 12 represented by Formula 1a where at least one of $R_5$ or $R_6$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure include derivatives of Compound 12 represented by Formula 1a where one of $R_5$ or $R_6$ is represented by Formula 1b, the one of $R_5$ or $R_6$ that is not represented by Formula 1b is hydrogen, each of $R_2$, $R_3$, $R_4$, and $R_7$ are hydrogen (H), and $R_{10}$ of Formula 1B is represented by Formula 2a.

In some embodiments, suitable compounds having an 8TQ structure include any one of Compounds 1-32 in Table 2.

According to some embodiments of the present invention, suitable compounds having an 8TQ structure may be a specific inhibitor of Rpn11 (i.e., as this term is defined herein, e.g., a compound that does not inhibit Csn5 or AMSH with the same potency as it inhibits Rpn11).

In some embodiments of the present invention, suitable compounds having an 8TQ structure may be specific inhibitors of Rpn11. These suitable specific Rpn11 inhibitors include derivatives of Compound 12 represented by Formula 1a where at least one of $R_3$, $R_4$, $R_5$, and/or $R_6$, is represented by Formula 1b, each of $R_2$ and $R_7$ are hydrogen (H), and $R_{10}$ of Formula 1b is represented by Formula 2a.

In some embodiments of the present invention suitable compounds having an 8TQ structure may be specific inhibitors of Rpn11. These suitable specific Rpn11 inhibitors include derivatives of Compound 12 represented by Formula 1a where one of $R_3$, $R_4$, $R_5$, and/or $R_6$, is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 2a.

In some embodiments of the present invention, suitable compounds having an 8TQ structure may be specific inhibitors of Rpn11. These suitable specific Rpn11 inhibitors include derivatives of Compound 12 represented by Formula 1a where at least one of $R_3$ or $R_4$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure may be specific inhibitors of Rpn11. These suitable specific Rpn11 inhibitors include derivatives of Compound 12 represented by Formula 1a where one of $R_3$ or $R_4$ is represented by Formula 1b, the one of $R_3$ or $R_4$ that is not represented by Formula 1b is hydrogen, each of $R_2$, $R_5$, $R_6$, and $R_7$ are hydrogen (H), and $R_{10}$ of Formula 1b is represented by Formula 2a.

In some embodiments of the present invention, suitable compounds having an 8TQ structure may be specific inhibitors of Rpn11. These suitable specific Rpn11 inhibitors include derivatives of Compound 12 represented by Formula 1a where at least one of $R_5$ or $R_6$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure may be specific inhibitors of Rpn11. These suitable specific Rpn11 inhibitors include derivatives of Compound 12 represented by Formula 1a where one of $R_5$ or $R_6$ is represented by Formula 1b, the one of $R_5$ or $R_6$ that is not represented by Formula 1b is hydrogen, each of $R_2$, $R_3$, $R_4$, and $R_7$ are hydrogen (H), and $R_{10}$ of Formula 1B is represented by Formula 2a.

In some embodiments, non-limiting examples of suitable specific inhibitors of Rpn11 include Compounds 1, 5, 9, 11, 12, 15, 17, 18, 19, 24, and 26, as shown in Table 2.

According to some embodiments of the present invention, the candidate compound of Formula 1a may be a specific in cellulo inhibitor of Rpn11 (i.e., as this term is defined herein, e.g., a compound that does not inhibit Csn5 or AMSH with the same potency as it inhibits Rpn11) and an inhibitor of proteasome protein degradation in cellulo.

According to some embodiments of the present invention, suitable having an 8TQ structure may be specific in cellulo inhibitors of Rpn11 (i.e., as this term is defined herein, e.g., a compound that does not inhibit Csn5 or AMSH with the same potency as it inhibits Rpn11).

In some embodiments of the present invention, suitable compounds having an 8TQ structure may be specific in cellulo inhibitors of Rpn11. These suitable specific in cellulo inhibitors of Rpn11 include derivatives of Compound 12 represented by Formula 1a where at least one of $R_3$, $R_4$, $R_5$, and/or $R_6$, is represented by Formula 1b, each of $R_2$ and $R_7$ are hydrogen (H), and $R_{10}$ of Formula 1b is represented by Formula 2a.

In some embodiments of the present invention suitable compounds having an 8TQ structure may be specific inhibitors of Rpn11. These suitable specific in cellulo inhibitors of Rpn11 include derivatives of Compound 12 represented by Formula 1a where one of $R_3$, $R_4$, $R_5$, and/or $R_6$, is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 2a.

In some embodiments of the present invention, suitable compounds having an 8TQ structure may be specific in cellulo inhibitors of Rpn11. These suitable specific in cellulo inhibitors of Rpn11 include derivatives of Compound 12 represented by Formula 1a where at least one of $R_3$ or $R_4$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure may be specific in cellulo inhibitors of Rpn11. These suitable specific in cellulo inhibitors of Rpn11 include derivatives of Compound 12 represented by Formula 1a where one of $R_3$ or $R_4$ is represented by Formula 1b, the one of $R_3$ or $R_4$ that is not represented by Formula 1b is hydrogen, each of $R_2$, $R_5$, $R_6$, and $R_7$ are hydrogen (H), and $R_{10}$ of Formula 1b is represented by Formula 2a.

In some embodiments of the present invention, suitable compounds having an 8TQ structure may be specific in cellulo inhibitors of Rpn11. These suitable specific in cellulo inhibitors of Rpn11 include derivatives of Compound 12 represented by Formula 1a where at least one of $R_5$ or $R_6$ is represented by Formula 1b, each of $R_2$ and $R_7$ are hydrogen (H), and $R_{10}$ of Formula 1b is represented by Formula 2a.

In some embodiments of the present invention, suitable compounds having an 8TQ structure may be in cellulo inhibitors of Rpn11. These suitable specific in cellulo inhibitors of Rpn11 include derivatives of Compound 12 represented by Formula 1a where one of $R_5$ or $R_6$ is represented by Formula 1b, the one of $R_5$ or $R_6$ that is not represented by Formula 1b is hydrogen, each of $R_2$, $R_3$, $R_4$, and $R_7$ are hydrogen (H), and $R_{10}$ of Formula 1B is represented by Formula 2a.

Nonlimiting examples of suitable specific in cellulo inhibitors include Compounds 1, 5, 12, and 24, as shown in Table 2.

TABLE 2

| Cmpd | Structure | Rpn11 IC$_{50}$ (µM) | Csn5 IC$_{50}$ (µM) | AMSH IC$_{50}$ (µM) | Ub$^{G76V}$-GFP IC$_{50}$ (µM) |
|---|---|---|---|---|---|
| 1 | 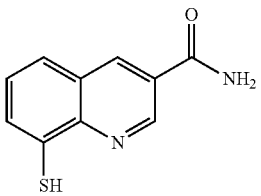 [SMILES: NC(=O)c1cnc2c(S)cccc2c1] | 1 | 15 | 1.2 | 1.2 |

TABLE 2-continued

| Cmpd | Structure | Rpn11 IC$_{50}$ (μM) | Csn5 IC$_{50}$ (μM) | AMSH IC$_{50}$ (μM) | Ub$^{G76V}$-GFP IC$_{50}$ (μM) |
|---|---|---|---|---|---|
| 2 | 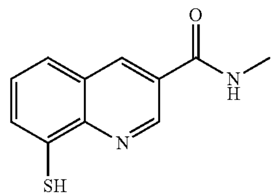 | 1.6 | 68 | 4.8 | 2.5 |
| 3 | 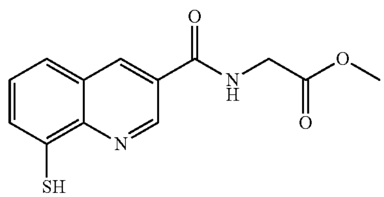 [SMILES: COC(=O)CNC(=O)c1cnc2c(S)cccc2c1] | 2.8 | 120 | 2.2 | 0.33 |
| 4 | 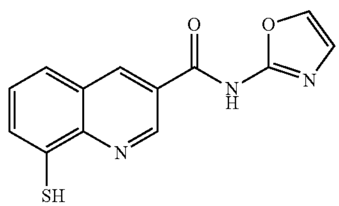 [SMILES: O=C(Nc1ncco1)c1cnc2c(S)cccc2c1] | 2.6 | 15 | 5 | >10 |
| 5 | 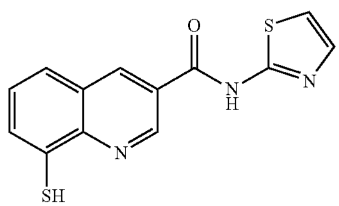 [SMILES: O=C(Nc1nccs1)c1cnc2c(S)cccc2c1] | 0.45 | 32 | 3.3 | 1.2 |
| 6 | 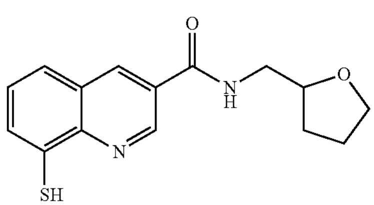 [SMILES: O=C(NCC1CCCO1)c1cnc2c(S)cccc2c1] | 4.6 | 41.3 | 6.8 | 1 |
| 7 | 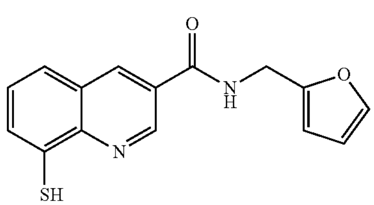 [SMILES: O=C(NCc1ccco1)c1cnc2c(S)cccc2c1] | 0.9 | 0.2 | 0.9 | 1 |
| 8 | 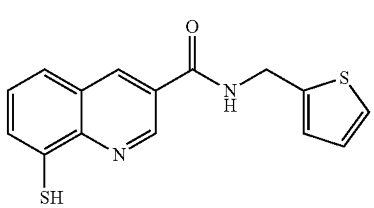 [SMILES: O=C(NCc1cccs1)c1cnc2c(S)cccc2c1] | 0.8 | 16 | 1.3 | 5 |

TABLE 2-continued

| Cmpd | Structure | Rpn11 IC$_{50}$ (μM) | Csn5 IC$_{50}$ (μM) | AMSH IC$_{50}$ (μM) | Ub$^{G76V}$-GFP IC$_{50}$ (μM) |
|---|---|---|---|---|---|
| 9 | 8-mercaptoquinoline-3-carboxamide with thiazol-2-ylmethyl | 0.5 | 23 | 7.8 | 2.9 |
| 10 | 8-mercaptoquinoline-3-carboxamide with 2-(furan-2-yl)ethyl | 1.2 | 6.9 | 1.7 | 1.4 |
| 11 | 8-mercaptoquinoline-3-carboxamide with 2-(thiophen-2-yl)ethyl | 0.3 | 4 | 1.3 | 5 |
| 12 | 8-mercaptoquinoline-3-carboxamide with 2-(thiazol-2-yl)ethyl | 0.34 | 30 | 4.5 | 0.57 |
| 13 | 8-mercaptoquinoline-3-carboxamide with pyridin-2-ylmethyl | 3.9 | 56.7 | 16.71 | >10 |
| 14 | 8-mercaptoquinoline-3-carboxamide with pyridin-3-ylmethyl | 3.1 | 128 | 3.52 | >10 |
| 15 | 8-mercaptoquinoline-3-carboxamide with pyridin-4-ylmethyl | 0.2 | 7 | 0.5 | >10 |

TABLE 2-continued
| Cmpd | Structure | Rpn11 IC$_{50}$ (μM) | Csn5 IC$_{50}$ (μM) | AMSH IC$_{50}$ (μM) | Ub$^{G76V}$-GFP IC$_{50}$ (μM) |
|---|---|---|---|---|---|
| 16 | 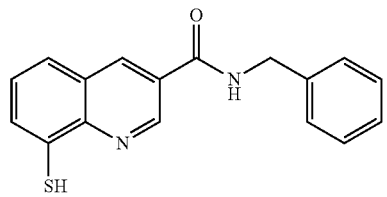 [SMILES: O=C(NCc1ccccc1)c1cnc2c(S)cccc2c1] | 1.1 | 11 | 15 | >10 |
| 17 | 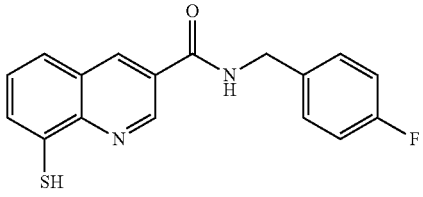 [SMILES: O=C(NCc1ccc(F)cc1)c1cnc2c(S)cccc2c1] | <0.2 | 18 | 0.85 | >10 |
| 18 | 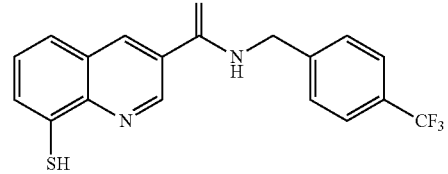 | 0.7 | >100 | 3.4 | >10 |
| 19 | 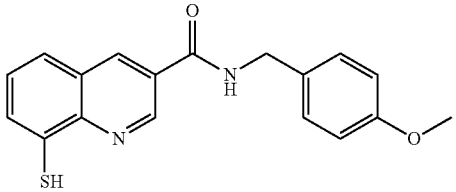 [SMILES: COc1ccc(CNC(=O)c2cnc3c(S)cccc3c2)cc1] | <0.2 | 0.5 | 0.6 | >10 |
| 20 | 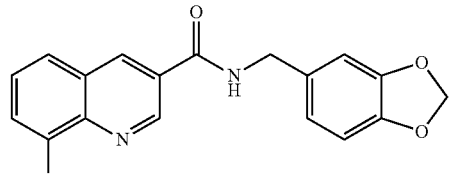 | 0.9 | 7 | <0.2 | >10 |
| 21 | 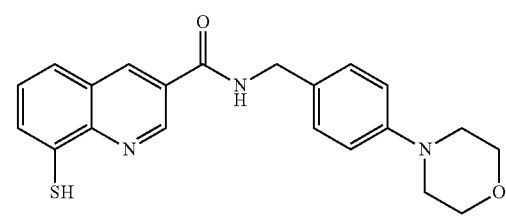 [SMILES: O=C(NCc1ccc(N2CCOCC2)cc1)c1cnc2c(S)cccc2c1] | 0.8 | 0.35 | 0.88 | >10 |
| 22 | 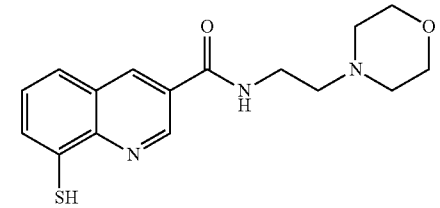 [SMILES: O=C(NCCN1CCOCC1)c1cnc2c(S)cccc2c1] | 6.4 | 99 | 25.4 | >10 |

TABLE 2-continued

| Cmpd | Structure | Rpn11 IC$_{50}$ (μM) | Csn5 IC$_{50}$ (μM) | AMSH IC$_{50}$ (μM) | Ub$^{G76V}$-GFP IC$_{50}$ (μM) |
|---|---|---|---|---|---|
| 23 | 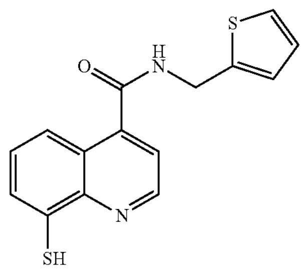 [SMILES: O=C(NCc1cccs1)c1ccnc2c(S)cccc12] | 1.2 | 19 | 2.27 | 1.1 |
| 24 | 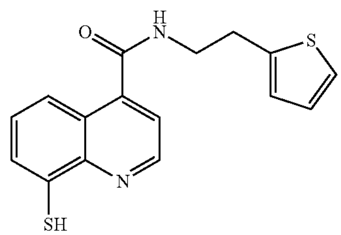 [SMILES: O=C(NCCc1cccs1)c1ccnc2c(S)cccc12] | 0.7 | 7.3 | 1 | 1.1 |
| 25 | 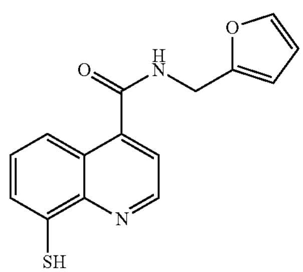 [SMILES: O=C(NCc1ccco1)c1ccnc2c(S)cccc12] | 2.2 | 4.9 | 2.2 | 2.4 |
| 26 | 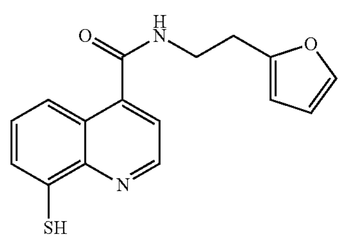 [SMILES: O=C(NCCc1ccco1)c1ccnc2c(S)cccc12] | 1 | 8 | 2.9 | 1.6 |
| 27 | 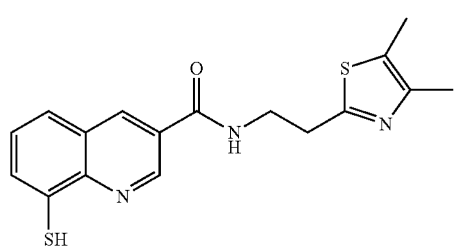 [SMILES: Cc1nc(CCNC(=O)c2cnc3c(S)cccc3c2)sc1C] | 0.5 | 4.4 | 0.5 | 0.54 |
| 28 | 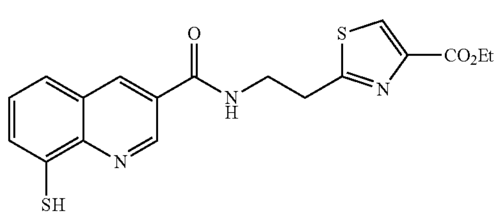 [SMILES: CCOC(=O)c1csc(CCNC(=O)c2cnc3c(S)cccc3c2)n1] | 0.70 | >20 | 0.7 | 0.8 |

TABLE 2-continued

| Cmpd | Structure | Rpn11 IC$_{50}$ (μM) | Csn5 IC$_{50}$ (μM) | AMSH IC$_{50}$ (μM) | Ub$^{G76V}$-GFP IC$_{50}$ (μM) |
|---|---|---|---|---|---|
| 29 | [8-mercaptoquinoline-3-carboxamide linked via ethyl to 4-methyl-thiazole-5-carboxylic acid] | 1.1 | >20 | 0.80 | 0.23 |
| 30 | [8-mercaptoquinoline-3-carboxamide linked via ethyl to 4-phenyl-thiazole] | 11.1 | 35 | >100 | >40 |
| 31 | [8-mercaptoquinoline-3-carboxamide linked via propyl to biotin amide] | 0.20 | 7.4 | 0.17 | 2.7 |
| 32 | [8-mercaptoquinoline-3-carboxamide linked via PEG3 to biotin amide] | 0.40 | 13.8 | 0.40 | 4.1 |

According to some embodiments of the present invention, a method for inhibiting Rpn11 includes administering one or more of the suitable 8TQ compounds represented by Formula 1a to a cell, a cell culture, or a cell in a subject (e.g, a human or animal). In some embodiments, the cancer cell is in vitro or in vivo.

In some embodiments, methods for inhibiting Rpn11 includes administering one or more of the suitable 8TQ compounds of Formula 1a where at least one of $R_2$, $R_3$, $R_4$, $R_5$, $R_6$, and/or $R_7$ of Formula 1a is a group represented by Formula 1b as defined herein according to embodiments of the present invention.

In some embodiments, a method for inhibiting Rpn11 includes administering one or more of the suitable 8TQ compounds represented by Formula 1a to a cell, a cell culture, or a cell in a subject, where for Formula 1a, at least one of $R_2$, $R_3$, $R_4$, $R_5$, $R_6$, and/or $R_7$ is represented by Formula 1b, and $R_{10}$ of Formula 1b is represented by Formula 4. In some embodiments, a method for inhibiting Rpn11 includes administering one or more of the suitable 8TQ compounds represented by Formula 1a to a cell, a cell culture, or a cell in a subject, where at least one of $R_3$, $R_4$, $R_5$, and/or $R_6$ is represented by Formula 1b, each of $R_2$ and $R_7$ are hydrogen (H), and $R_{10}$ of Formula 1b is represented by Formula 4.

In some embodiments, a method for inhibiting Rpn11 includes administering one or more of the suitable 8TQ compounds represented by Formula 1a to a cell, a cell culture, or a cell in a subject, where for Formula 1a one of $R_3$, $R_4$, $R_5$, and/or $R_6$ is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 4.

In some embodiments, a method for inhibiting Rpn11 includes administering one or more of the derivatives of Compound 12 represented by Formula 1a to a cell, a cell culture, or a cell in a subject, where for Formula 1a, at least one of $R_2$, $R_3$, $R_4$, $R_5$, $R_6$, and/or $R_7$ is represented by Formula 1b, and $R_{10}$ of Formula 1b is represented by Formula 2a (a derivative of Formula 2). Any variable not specified for Formula 1a, 1b, 2, and 2a are as defined herein for each respective formula.

In some embodiments of the present invention, a method for inhibiting Rpn11 includes administering one or more of the derivatives of Compound 12 represented by Formula 1a to a cell, a cell culture, or a cell in a subject, where for Formula 1a, at least one of $R_3$, $R_4$, $R_5$, and/or $R_6$, is represented by Formula 1b, each of $R_2$ and $R_7$ are hydrogen (H), and $R_{10}$ of Formula 1b is represented by Formula 2a.

In some embodiments of the present invention, a method for inhibiting Rpn11 includes administering one or more of the derivatives of Compound 12 represented by Formula 1a to a cell, a cell culture, or a cell in a subject, where for Formula 1a, one of $R_3$, $R_4$, $R_5$, and/or $R_6$, is represented by Formula 1b, each of $R_2$ and $R_7$ are hydrogen (H), each of $R_3$, $R_4$, $R_5$, and/or $R_6$ that is not represented by Formula 1b is hydrogen, and $R_{10}$ of Formula 1b is represented by Formula 2a.

In some embodiments of the present invention, a method for inhibiting Rpn11 includes administering one or more of the derivatives of Compound 12 represented by Formula 1a to a cell, a cell culture, or a cell in a subject, where for Formula 1a, at least one of $R_3$ or $R_4$ is represented by Formula 1b, each of $R_2$ and $R_7$ are hydrogen (H), and $R_{10}$ of Formula 1b is represented by Formula 2a.

In some embodiments of the present invention, a method for inhibiting Rpn11 includes administering one or more of the derivatives of Compound 12 represented by Formula 1a to a cell, a cell culture, or a cell in a subject, where for Formula 1a, one of $R_3$ or $R_4$ is represented by Formula 1b, the one of $R_3$ or $R_4$ that is not represented by Formula 1b is hydrogen, each of $R_2$, $R_5$, $R_6$, and $R_7$ are hydrogen (H), and $R_{10}$ of Formula 1b is represented by Formula 2a.

In some embodiments of the present invention, a method for inhibiting Rpn11 includes administering one or more of the derivatives of Compound 12 represented by Formula 1a to a cell, a cell culture, or a cell in a subject, where for Formula 1a, at least one of $R_5$ or $R_6$ is represented by Formula 1b, each of $R_2$ and $R_7$ are hydrogen (H), and $R_{10}$ of Formula 1b is represented by Formula 2a.

In some embodiments of the present invention, a method for inhibiting Rpn11 includes administering one or more of the derivatives of Compound 12 represented by Formula 1a to a cell, a cell culture, or a cell in a subject, where for Formula 1a, one of $R_5$ or $R_6$ is represented by Formula 1b, the one of $R_5$ or $R_6$ that is not represented by Formula 1b is hydrogen, each of $R_2$, $R_3$, $R_4$, and $R_7$ are hydrogen (H), and $R_{10}$ of Formula 1B is represented by Formula 2a.

In some embodiments of the present invention, a method for inhibiting Rpn11 includes administering one or more of Compounds 1, 5, 12, or 24 to a cell, cell culture, or a cell in a subject.

The following Examples are presented for illustrative purposes only, and do not limit the scope or content of the present application.

EXAMPLES

Example 1

Starting materials and solvents were purchased from commercial suppliers (Sigma-Aldrich, BioBlocks, Alfa Aesar, Fisher, etc.) and used as received. Microwave synthesis reactions were performed in 10 mL or 35 mL microwave vials using a CEM Discover S reactor. Column chromatography was performed using a Teledyne ISCO CombiFlash Rf system with prepacked silica cartridges. $^1H/^{13}C$ NMR spectra were recorded at ambient temperature on a 400 or 500 Varian FT-NMR instrument located in the Department of Chemistry and Biochemistry at the University of California, San Diego. Mass spectra were obtained at the Molecular Mass Spectrometry Facility in the Department of Chemistry and Biochemistry at the University of California, San Diego.

Example 2

Synthesis and Activity of 8TQ Derivatives. A sublibrary of compounds with simple modifications to the 8TQ scaffold was prepared in an effort to probe for possible hydrophobic (methyl groups) and hydrophilic (acids and esters groups) contacts within the active site, as well as to determine the best positions on the 8TQ ring to add substituents for subsequent rounds of derivatization. Functionalization of the 8TQ fragment was achieved largely via the Skraup and Doubner-Von Miller reactions using aniline derivatives as starting materials. Compounds 9a-11c of Scheme 1 below were synthesized starting with 2-fluoroaniline with the quinoline ring forming upon addition of a methyl-α,β-unsaturated aldehyde in the presence of aqueous HCl (Scheme 1). The 4-methyl quinoline analog was synthesized in similar fashion, by combining 2-fluoroaniline with an α,β-unsaturated ketone (Scheme 1).

Scheme 1. Synthesis of 2-, 3-, and 4-methyl-8-thioquinoline (apolar) derivatives of 8TQ.

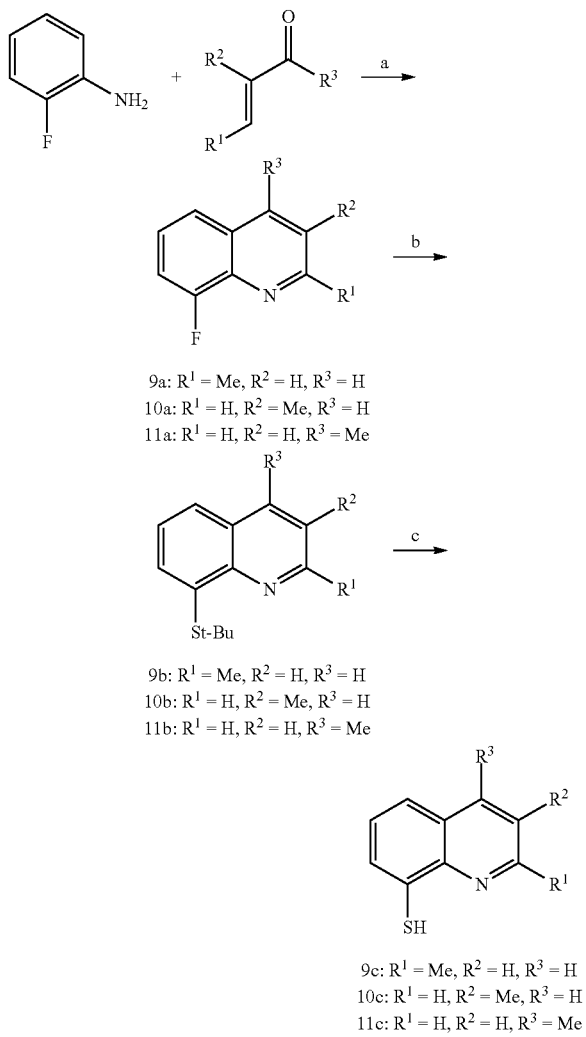

The reactants of Scheme 1 are: (a) Toluene, 6M HCl, at 110° C.; (b) t-BuSH, NaH, DMF, at 140° C.; (c) 12M HCl, at 100° C.

Compounds 12a-13c were obtained by starting with methyl functionalized 2-chloro or 2-fluoroaniline in the presence of glycerol utilizing nitrobenzene as the solvent and oxidant (Scheme 2). Substitution of the resulting methyl-8-fluoro or methyl-8-choroquinoline to obtain the thiol functionality was obtained following the general reaction depicted in Scheme 2 for compound 7c. Synthesis of compound 7c.

Scheme 2.

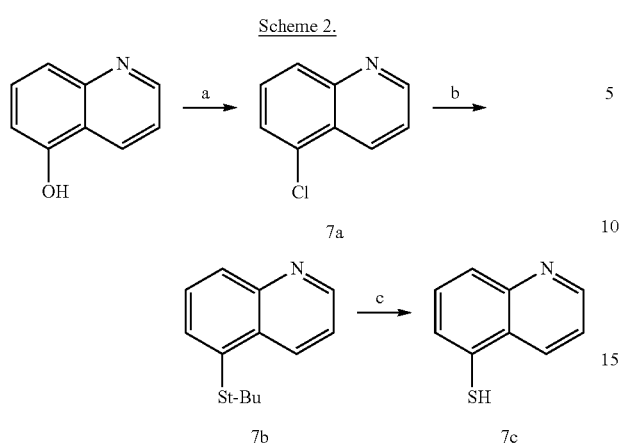

The reactants for Scheme 2 are: (a) POCl₃, at 100° C.; (b) t-BuSH, NaH, DMF, at 140° C.; (c) 12M HCl, at 100° C.

Example 3

Scheme 3: Synthesis of 2- and 3-carboxyl-8-thioquinoline (polar) derivatives.

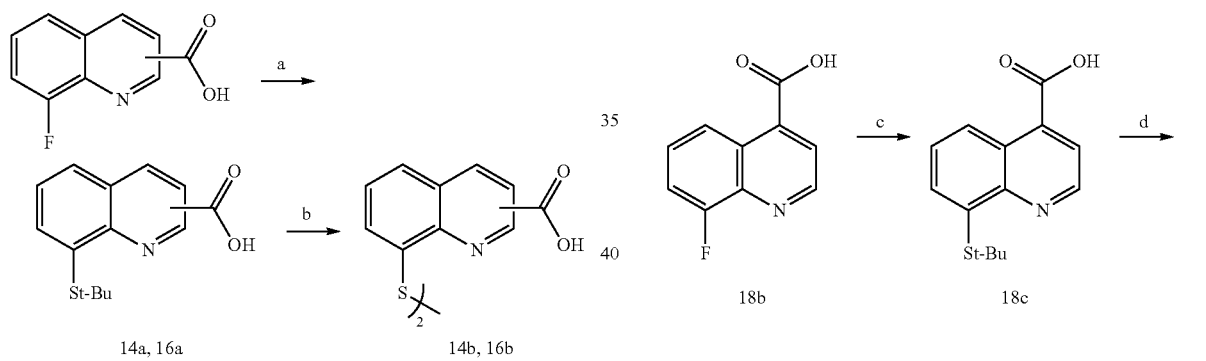

The reactants of Scheme 3 are: (a) t-BuSH, NaH, DMF, at 140° C.; (b) 12M HCl, at 100° C.

Compounds 14b and 16b were synthesized starting from commercially available 2- or 3-carboxyl-8-fluoroquinoline as detailed in Scheme 3. The 2-, 3-, and 4-carboxylate-8-thioquinoline compounds were coupled to amines via the assistance of carbodiimidazole (CDI) or 1-[bis(dimethylamino)methylene]-1H-1,2,3-triazolo[4,5-b]pyridinium 3-oxid hexafluorophosphate (HATU) coupling reagents. Alkyl amines were coupled through the use of CDI at room temperature; however, less nucleophilic amines (aromatic) were coupled with HATU and heating.

Screening of 2-carboxyl-8-thioquinoline (polar) derivatives including compounds 9c, 14b, dimethyl 8,8'-disulfanediylbis(quinoline-2-carboxylate), 8,8'-disulfanediylbis(N-(thiophen-2-ylmethyl)quinoline-2-carboxamide), and 8,8'-Disulfanediylbis(N-benzylquinoline-2-carboxamide), synthesized as described herein, demonstrated that functionalization at the 2-position was not well tolerated, as all of these compounds were consistently less active than 8TQ.

Example 4

Scheme 4. Synthesis of 4-carboxyl-8-thioquinoline

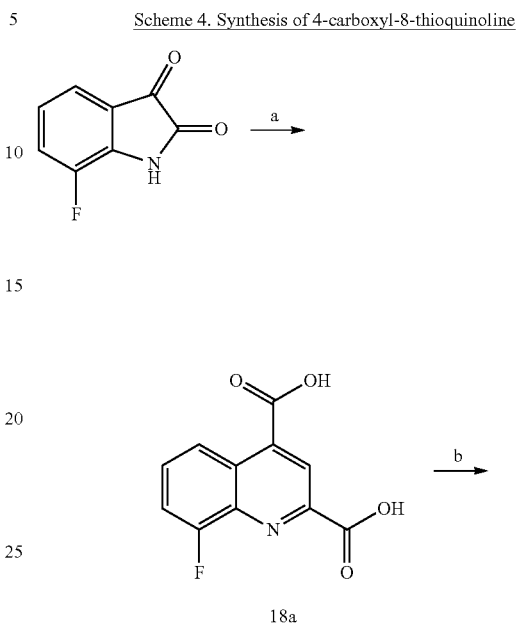

The reactants of Scheme 4 are: (a) Sodium Pyruvate, 1M NaOH, at 55° C.; (b) H₂O, at 200° C.; (c) t-BuSH, NaH, DMF, at 140° C.; (d) 12M HCl, at 100° C.

Compound 18d was obtained via a Pfitzinger ring expansion reaction of 7-fluoroisatin and pyruvate under basic conditions to yield 18a. This was decarboxylated under aqueous conditions to afford 18b, which then yielded 18d over two steps (Scheme 4)

Example 5

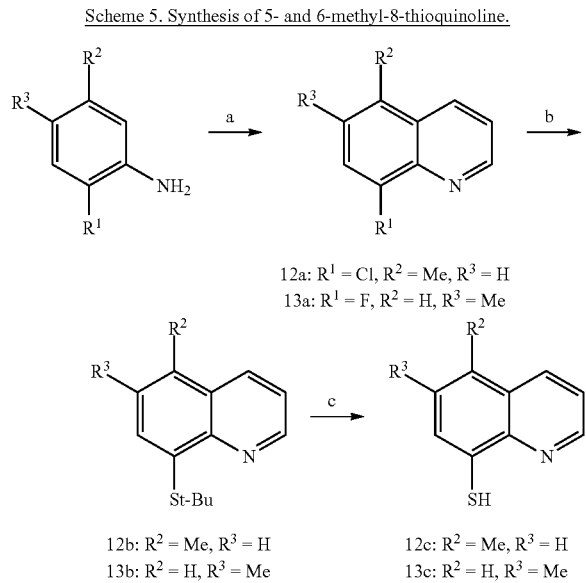

Scheme 5. Synthesis of 5- and 6-methyl-8-thioquinoline.

12a: R¹ = Cl, R² = Me, R³ = H
13a: R¹ = F, R² = H, R³ = Me

12b: R² = Me, R³ = H
13b: R² = H, R³ = Me

12c: R² = Me, R³ = H
13c: R² = H, R³ = Me

The reactants of Scheme 5 are: (a) Glycerol, Nitrobenzene, at 150° C.; (b) t-BuSH, NaH, DMF, at 140° C.; (c) 12M HCl, at 100° C.

It is noted that all of the aforementioned compounds in Examples 2-5 were isolated as disulfide dimers, as evidenced by mass spectrometry. Under the assay conditions, which contained 1 mM of dithiothreitol (DTT) as a reductant, the disulfides were reduced to the monomeric active species.

Example 6

2,2-Dimethyl-5-((pyridin-3-ylamino)methylene)-1,3-dioxane-4,6-dione (8a). To a preheated (~100° C.) mixture of 3-aminopyridine (0.37 g, 4.0 mmol) and 2,2-dimethyl-[1,3]dioxane-4,6-dione (Meldrum's acid, 0.69 g, 4.8 mmol) was added triethyl orthoformate (4.0 mL, 24.0 mmol). The solution was stirred at 100° C. for 2 h. The reaction proceeded by changing color from yellow to wine red accompanying the formation of yellow precipitate. After cooling to room temperature, the excess liquid of triethyl orthoformate was removed via vacuum distillation. The resulting solid was purified via silica gel chromatography using a gradient of 70 to 100% EtOAc in hexanes. Yield=0.72 g (72%). $^1$H NMR (400 MHz, CDCl$_3$): δ 11.25 (d, J=10.4 Hz, 1H), 8.63 (d, J=14.00 Hz, 1H), 8.61 (d, J=3.2 Hz, 1H), 8.55 (dd, J=4.8 Hz, J=1.6 Hz, 1H), 7.61 (d, J=8.0 Hz, 1H), 7.41 (dd, J=8.20, 4.2 Hz, 1H), 1.77 (s, 6H). $^{13}$C NMR (100 MHz, CDCl$_3$): δ 165.2, 163.0, 152.9, 147.6, 140.6, 134.6, 124.9, 124.1, 105.2, 88.5, 26.9. ESI-MS (+): m/z 248.90 [M+H]$^+$.

Example 7

1,5-Naphthyridin-4-ol (8b). To a flask containing 8a (2.6 g, 10.4 mmol) under nitrogen atmosphere was added Dowtherm A (150 mL) and placed in a preheated oil bath (250° C.) and stirred at reflux for 1 h. During the reaction, the color of the solution changed from orange yellow to dark brown. After cooling down to room temperature, the reaction solution was filtered to isolate solid product. The solid was rinsed with diphenyl ether and acetone to give the desired product as a dark solid. Yield=1.14 g (75%). $^1$H NMR (400 MHz, CD$_3$OD+one drop TFA): δ 9.07 (d, J=4.8 Hz, 1H), 8.72 (d, J=8.8 Hz, 1H), 8.61 (d, J=7.2 Hz, 1H), 8.22 (dd, J=8.8 Hz, J=4.8 Hz, 1H), 7.07 (d, J=7.2 Hz, 1H). $^{13}$C NMR (125 MHz, CD$_3$OD+one drop TFA): δ 172.3, 147.5, 145.5, 138.6, 134.8, 134.4, 130.1, 112.2. ESI-MS (+): m/z 147.29 [M+H]$^+$.

Example 8

4-Chloro-1,5-naphthyridine (8c). To a solution of 8b (0.8 g, 5.47 mmol) in toluene (20 mL) was added POCl$_3$ (1.02 mL, 10.95 mmol) at room temperature. The solution was stirred at 110° C. for 2 h, then allowed to cool to room temperature, which caused formation of a precipitate. The solution and dark solid was quenched with sat. NaHCO$_3$ and extracted with EtOAc. The combined organic layers were dried over anhydrous Na$_2$SO$_4$, then filtered and concentrated. The residue was purified via silica gel chromatography using a gradient of 20 to 40% EtOAc in CH$_2$Cl$_2$. Yield=0.37 g (41%). $^1$H NMR (400 MHz, CDCl$_3$): δ 8.92 (dd, J=4.4, 1.2 Hz, 1H), 8.69 (d, J=4.8 Hz, 1H), 8.26 (dd, J=8.8, 1.6 Hz, 1H), 7.60 (d, J=8.0 Hz, 1H), 7.56 (dd, J=8.4, 4.0 Hz, 1H). $^{13}$C NMR (100 MHz, CDCl$_3$): δ 151.4, 151.3, 150.5, 144.7, 143.9, 140.7, 137.8, 125.2, 124.3. ESI-MS (+): m/z 165.28 [M+H]$^+$.

Example 9

4-((4-Methoxybenzyl)thio)-1,5-naphthyridine (8d). To a solution of 8c (900 mg, 5.47 mmol) in DMF (30.0 mL) was added PMBSH (4-methoxyphenyl)methanethiol, 1.1 mL, 8.20 mmol) at room temperature. The solution was stirred for 2 h, then quenched with MeOH and concentrated under reduced pressure. The resulting residue was diluted with H$_2$O and neutralized with 1N HCl to pH~8. The aqueous solution was extracted with EtOAc. The combined organic layers were dried over anhydrous Na$_2$SO$_4$, then filtered and concentrated. The crude product was purified via silica gel chromatography using a gradient of 25 to 70% EtOAc in hexanes. Yield=1.07 g (70%). $^1$H NMR (400 MHz, CDCl$_3$): δ 8.90 (dd, J=4.4, 1.6 Hz, 1H), 8.69 (d, J=4.8 Hz, 1H), 8.33 (dd, J=8.4, 1.6 Hz, 1H), 7.63 (dd, J=8.4, 4.8 Hz, 1H), 7.39 (d, J=9.2 Hz, 2H), 7.35 (d, J=4.8 Hz, 1H), 6.86 (dd, J=8.8 Hz, 2H), 4.24 (s, 2H), 3.77 (s, 3H). $^{13}$C NMR (125 MHz, CDCl$_3$): δ 159.2, 151.4, 150.1, 149.5, 142.6, 141.7, 137.7, 130.1, 130.1, 126.9, 125.0, 118.1, 114.3, 55.4, 34.8. ESI-MS (+): m/z 283.05 [M+H]$^+$.

Example 10

1,5-Naphthyridine-4-thiol (8e). To a solution of 8d (0.7 g, 2.48 mmol) in TFA (20 mL) was added m-cresol (1.3 mL, 12.41 mmol) at room temperature. The solution was then stirred at reflux for 16 h and then allowed to cool. The resulting solution was concentrated and diluted with the EtOAc. The solution was neutralized with sat. NaHCO$_3$, which resulted in the formation of an orange red precipitate. The solid was collected via filtration and washed with water and acetone to give the desired product. Yield=0.38 g, (94%). $^1$H NMR (400 MHz, CDCl$_3$): δ 8.70-8.63 (m, 1H), 8.03 (dd, J=7.8, 2.2 Hz, 1H), 7.95 (d, J=4.8 Hz, 1H), 7.46 (dd, J=8.2, 4.2 Hz, 1H), 7.41 (d, J=5.2 Hz, 1H). $^{13}$C NMR (100 MHz, CDCl$_3$): δ 174.2, 148.4, 147.2, 146.7, 143.4, 137.42, 128.2, 122.8. ESI-MS (+): m/z 163.19 [M+H]$^+$.

Example 11

8-Fluoro-2-methylquinoline (9a). To a solution of 2-fluoroaniline (1 g, 9 mmol) in toluene (40 mL) was added 6M HCl (12 mL) and crotonaldehyde (1.47 mL, 1.8 mmol). The heterogeneous mixture was stirred at 110° C. for 2 h. The aqueous layer was separated, neutralized to pH 9, and extracted with EtOAc (3×50 mL). The combined organic layers were dried and concentrated under reduced pressure. The crude material was purified via silica gel column chromatography using a gradient of 0 to 100% EtOAc in hexanes. Yield=0.71 g (49%). $^1$H NMR (400 MHz, DMSO-d$^6$): δ 8.29 (d, J=9.5 Hz, 1H), 7.71 (d, J=7.0 Hz, 1H), 7.56-7.40 (m, 3H), 2.66 (s, 3H). ESI-MS (+): m/z 162.2 [M+H]$^+$.

Example 12

8-(tert-Butylthio)-2-methylquinoline (9b). To a solution of 9a (0.195 g, 1.21 mmol) in DMF (20 mL) was added NaH (0.097 g, 4.04 mmol) and tert-butylthiol (272 µL, 2.42 mmol) under nitrogen atmosphere. The solution was stirred at 140° C. for 18 h. Then the solution was evaporated to dryness and the crude material was purified via silica gel column chromatography using a gradient of 0 to 100% EtOAc in hexanes. Yield=0.22 g (77%). $^1$H NMR (400 MHz, CDCl$_3$): δ 8.74 (d, J=8.3 Hz, 1H), 8.27 (dd, J=7.2, 1.3 Hz, 1H), 8.17-8.04 (m, 1H), 7.81 (t, J=7.8 Hz, 1H), 7.75 (d, J=8.4 Hz, 1H), 3.59 (s, 3H), 1.43 (s, 9H). ESI-MS(+): m/z 231.91 [M+H]$^+$.

Example 13

2-Methylquinoline-8-thiol (9c). A solution of 9b (0.04 g, 0.17 mmol) in conc. HCl (11 mL) was stirred at 90° C. for 19 h. The solution was neutralized to pH 9-10 and extracted EtOAc (3×10 mL). The combined organic layers were dried and concentrated under reduced pressure. The crude material was recrystallized from EtOH. Yield=0.02 g (66%). $^1$H NMR (500 MHz, CDCl$_3$): δ 8.07 (d, J=8.4 Hz, 1H), 7.85 (d, J=7.5 Hz, 1H), 7.58 (d, J=8.0 Hz, 1H), 7.41-7.30 (m, 2H), 2.85 (s, 3H). APCI-MS(−): m/z 174.10 [M−H]$^-$.

Example 14

8-Fluoro-3-methylquinoline (10a). To a solution of 2-fluoroaniline (1.0 g, 9 mmol) in toluene (40 mL) was added 6M HCl (12 mL) and methacrolein (1.5 mL, 1.8 mmol). The heterogeneous mixture was stirred at 110° C. for 2.5 h. The aqueous layer was separated, neutralized to pH 9 and extracted with EtOAc (3×50 mL). The combined organic layers were dried and concentrated under reduced pressure. The crude material was purified via silica gel column chromatography using a gradient of 0 to 100% EtOAc in hexanes. Yield=0.65 g (45%). $^1$H NMR (500 MHz, CDCl$_3$): δ 8.53 (d, J=2.3 Hz, 1H), 7.56 (s, 1H), 7.22-7.17 (m, 1H), 7.17-7.10 (m, 1H), 7.08-6.98 (m, 1H), 2.22-2.21 (s, 3H). ESI-MS(+): m/z 162.19 [M+H]$^+$.

Example 15

8-(tert-Butylthio)-3-methylquinoline (10b). To a solution of 10a (0.5 g, 3.1 mmol) in DMF (50 mL) was added NaH (0.25 g, 10.3 mmol) and tert-butylthiol (698 µL, 6.2 mmol) under nitrogen atmosphere. The solution was stirred at 140° C. for 18 h. Then the solution was evaporated to dryness and the crude material purified via silica gel column chromatography using a gradient of 0 to 100% EtOAc in hexanes. Yield=0.56 g (78%). $^1$H NMR (500 MHz, CDCl$_3$): δ 8.90 (d, J=2.3 Hz, 1H), 7.96 (dd, J=7.2, 1.5 Hz, 1H), 7.92 (d, J=1.1 Hz, 1H), 7.74 (dd, J=8.2, 1.5 Hz, 1H), 7.47 (dd, J=8.1, 7.2 Hz, 1H), 2.53 (s, 3H), 1.37 (s, 9H). ESI-MS(+): m/z 231.92 [M+H]$^+$.

Example 16

3-Methylquinoline-8-thiol (10c). A solution of 10b (0.08 g, 0.35 mmol) in conc. HCl (25 mL) was stirred at 90° C. for 19 h. The resulting solution was neutralized to pH 9 with NaOH and extracted with EtOAc (3×10 mL). The combined organic layers were dried and concentrated under reduced pressure. The crude material was purified via silica gel column chromatography using a gradient of 0 to 100% EtOAc in hexanes. Yield=0.02 g (33%). $^1$H NMR (500 MHz, CDCl$_3$): δ 8.73 (d, J=8.4 Hz, 1H), 7.85 (d, J=7.5 Hz, 1H), 7.60 (d, J=8.0 Hz, 1H), 7.47-7.45 (m, 1H), 7.35-7.31 (m, 1H), 5.58 (s, 1H), 2.48 (s, 3H). ESI-MS(+): m/z 176.16 [M+H]$^+$.

Example 17

8-Fluoro-4-methylquinoline (11a). To a solution of 2-fluoroaniline (1.0 g, 9 mmol) in toluene (40 mL) was added 6M HCl (12 mL) and methyl vinyl ketone (1.5 mL, 1.8 mmol). The heterogeneous mixture was stirred at 110° C. for 16 h. The aqueous layer was separated, neutralized to pH 9 with 6M NaOH and extracted with CH$_2$Cl$_2$ (3×50 mL). The combined organic layers were dried and concentrated under reduced pressure. The crude material was purified via silica gel column chromatography using a gradient of 0 to 100% EtOAc in hexanes. Yield=0.4 g (28%). $^1$H NMR (500 MHz, DMSO-d$^6$): δ 8.74 (d, J=4.4 Hz, 1H), 7.83-7.77 (m, 1H), 7.57-7.46 (m, 2H), 7.39 (dd, J=4.3, 1.0 Hz, 1H), 2.61 (s, 3H). ESI-MS(+): m/z 162.23 [M+H]$^+$.

Example 18

8-(tert-Butylthio)-4-methylquinoline (11b). To a solution of 11a (255 mg, 1.58 mmol) in DMF (25 mL) was added NaH (0.13 g, 5.29 mmol) and tert-butylthiol (356 µL, 3.16 mmol) under nitrogen atmosphere. The solution was stirred at 140° C. for 18 h. Then the solution was evaporated to dryness and the crude material was purified via silica gel column chromatography using a gradient of 0 to 100% EtOAc in hexanes. Yield=0.2 g (55%). $^1$H NMR (500 MHz, CDCl$_3$): δ 8.88 (d, J=4.3 Hz, 1H), 8.05-7.93 (m, 2H), 7.50 (dd, J=8.4, 7.2 Hz, 1H), 7.22 (dd, J=4.3, 1.0 Hz, 1H), 2.69 (s, 3H), 1.36 (s, 9H). ESI-MS(+): m/z 231.90 [M+H]$^+$.

Example 19

4-Methylquinoline-8-thiol (11c). A solution of 11b (0.08 g, 0.35 mmol) in conc. HCl (25 mL) was stirred at 90° C. for 19 h. The crude material was neutralized to pH 9 with NaOH and extracted with EtOAc (3×50 mL). The combined organic layers were dried and concentrated under reduced pressure. The crude material was purified via silica gel column chromatography using a gradient of 0 to 100% EtOAc in hexanes. Yield=0.02 g (30%). $^1$H NMR (500 MHz, CDCl$_3$): δ 8.76 (d, J=4.4 Hz, 1H), 7.76-7.66 (m, 2H), 7.39 (dd, J=8.4, 7.3 Hz, 1H), 7.25 (dd, J=4.4, 1.0 Hz, 1H), 2.69 (s, 3H). ESI-MS(+): m/z 176.17 [M+H]$^+$.

Example 20

8-Chloro-5-methylquinoline (12a). To a solution of 2-chloro-5-methylaniline (1 g, 14.1 mmol) in 75% sulfuric acid (8 mL) was added nitrobenzene (1.44 mL, 14.1 mmol) and glycerol (2.06 mL, 28.2 mmol). The heterogeneous mixture was stirred at 150° C. for 2 h. This was allowed to cool, then H$_2$O was added to the mixture and extracted with EtOAc (2×50 mL). The combined organic layers were dried and concentrated under reduced pressure. The crude material was purified via silica gel column chromatography using a gradient of 0 to 100% EtOAc in hexanes. Yield=1.0 g (40%). $^1$H NMR (500 MHz, CDCl$_3$): δ 9.04 (dd, J=4.2, 1.7 Hz, 1H), 8.32 (dd, J=8.5, 1.7 Hz, 1H), 7.71 (d, J=7.7 Hz, 1H), 7.49 (dd, J=8.5, 4.2 Hz, 1H), 7.28 (dd, J=7.8, 0.9 Hz, 1H), 2.65 (d, J=1.0 Hz, 3H). ESI-MS(+): m/z 178.21 [M+H]$^+$.

Example 21

8-(tert-Butylthio)-5-methylquinoline (12b). To a solution of 12a (1 g, 5.62 mmol) in DMF (100 mL) was added NaH (0.45 g, 18.8 mmol) and tert-butylthiol (1.26 mL, 3.16 mmol) under nitrogen atmosphere. The solution was stirred at 140° C. for 18 h. Then the solution was evaporated to dryness and the crude material purified via silica gel column chromatography using a gradient of 0 to 100% EtOAc in hexanes. Yield=0.19 g (14%). $^1$H NMR (500 MHz, CDCl$_3$): δ 9.05 (dd, J=4.2, 1.7 Hz, 1H), 8.34 (dd, J=8.5, 1.7 Hz, 1H), 7.72 (d, J=7.6 Hz, 1H), 7.50 (dd, J=8.5, 4.2 Hz, 1H), 7.29 (dd, J=7.6, 1.0 Hz, 1H), 2.66 (d, J=1.0 Hz, 3H), 1.34 (s, 9H). ESI-MS(+): m/z 231.91 [M+H]$^+$.

Example 22

5-Methylquinoline-8-thiol (12c). A solution of 12b (0.08 g, 0.35 mmol) in conc. HCl (25 mL) was stirred at 100° C. for 19 h. The resulting solution was neutralized to pH 9 with NaOH and extracted with EtOAc (3×50 mL). The combined organic layers were dried and concentrated under reduced pressure. The crude material was purified via silica gel column chromatography using a gradient of 0 to 100% EtOAc in hexanes. Yield=0.05 g (81%). $^1$H NMR (500 MHz, CDCl$_3$): δ 8.94 (dd, J=4.3, 1.8 Hz, 1H), 8.09 (dd, J=8.3, 1.8 Hz, 1H), 7.79 (d, J=1.8 Hz, 1H), 7.45 (dd, J=8.3, 4.3 Hz, 1H), 7.38 (s, 1H), 2.39 (s, 3H).

Example 23

8-Fluoro-6-methylquinoline (13a). To a solution of 2-fluoro-6-methylaniline (0.5 g, 4.0 mmol) in 75% sulfuric acid (4 mL) was added nitrobenzene (409 µL, 4.0 mmol) and glycerol (588 µL, 8.0 mmol). The heterogeneous mixture was stirred at 150° C. for 3 h. This was allowed to cool, then H$_2$O was added to the mixture and extracted twice with EtOAc (2×50 mL). The combined organic layers were dried and concentrated under reduced pressure. The crude material was purified via silica gel column chromatography using a gradient of 0 to 100% EtOAc in hexanes. Yield=0.17 g (27%). $^1$H NMR (500 MHz, CDCl$_3$): δ 8.79 (dd, J=4.2, 1.6 Hz, 1H), 7.99 (d, J=8.4 Hz, 1H), 7.92 (s, 1H), 7.34 (dd, J=8.4, 4.2 Hz, 1H), 7.15 (dd, J=11.5, 1.8 Hz, 1H), 2.43 (d, J=1.0 Hz, 3H). ESI-MS(+): m/z 162.19 [M+H]$^+$.

Example 24

8-(tert-Butylthio)-6-methylquinoline (13b). To a solution of 13a (0.14 g, 0.87 mmol) in DMF (14 mL) was added NaH (0.07 g, 2.91 mmol) and tert-butylthiol (196 µL, 1.74 mmol) under nitrogen atmosphere. The solution was stirred at 140° C. for 18 h. Then the solution was evaporated to dryness and the crude material purified via silica gel column chromatography using a gradient of 0 to 100% EtOAc in hexanes. Yield=0.16 g (78% yield). $^1$H NMR (500 MHz, CDCl$_3$): δ 8.98 (dd, J=4.2, 1.8 Hz, 1H), 8.06 (dd, J=8.2, 1.8 Hz, 1H), 7.89 (d, J=2.0 Hz, 1H), 7.58 (d, J=1.0 Hz, 1H), 7.37 (dd, J=8.2, 4.2 Hz, 1H), 2.54 (s, 3H), 1.37 (s, 9H). ESI-MS(+): m/z 231.91 [M+H]$^+$.

Example 25

6-Methylquinoline-8-thiol (13c). A solution of 13b (0.08 g, 0.35 mmol) in conc. HCl (25 mL) was stirred at 100° C. for 19 h. The crude material was neutralized to pH 9 with NaOH and extracted with EtOAc (3×50 mL). The combined organic layers were dried and concentrated under reduced pressure. The crude material was purified via silica gel column chromatography using a gradient of 0 to 100% EtOAc in hexanes. Yield=0.03 g (46%). $^1$H NMR (400 MHz, CDCl$_3$): δ 8.84 (dd, J=4.3, 1.6 Hz, 1H), 8.03 (dd, J=8.2, 1.6 Hz, 1H), 7.55 (d, J=1.8 Hz, 1H), 7.38 (dd, J=8.2, 4.2 Hz, 1H), 7.31 (d, J=0.9 Hz, 1H), 5.61 (s, 1H), 2.46 (s, 3H). ESI-MS(+): m/z 176.17 [M+H]$^+$.

Example 26

8-(tert-Butylthio)quinoline-2-carboxylic acid (14a). To a solution of 8-fluoroquinoline-2-carboxylic acid (0.42 g, 2.19 mmol) in DMF (40 mL) was added NaH (0.18 g, 7.29 mmol) and tert-Butylthiol (495 µL, 4.4 mmol) under nitrogen atmosphere. The solution was stirred at 140° C. for 18 h. The solution was evaporated to dryness and the crude material was taken in water and acidified with 1M HCl until a precipitate was formed (pH 2). The precipitate was filtered and dried under vacuum. Yield=0.45 g (78%). $^1$H NMR (400 MHz, CDCl$_3$): δ 8.42 (dd, J=8.5, 2.4 Hz, 1H), 8.32 (dd, J=6.6, 3.7 Hz, 1H), 8.12 (d, J=6.8 Hz, 1H), 7.94 (d, J=7.2 Hz, 1H), 7.70-7.62 (m, 1H), 1.35-1.30 (m, 9H). ESI-MS(+): m/z 261.96 [M+H]$^+$.

Example 27

8,8'-Disulfanediylbis(quinoline-2-carboxylic acid) (14b). A solution of 14a (0.24 g, 0.92 mmol) in conc. HCl (40 mL) was stirred at 110° C. for 12 h. The crude material was neutralized to pH 9 and washed with EtOAc (2×50 mL). The aqueous layer was then acidified to pH 2-3 and the precipitate was filtered off and dried under vacuum. The product was isolated as a disulfide dimer as evidenced by mass spectrometry. Yield=0.15 g (80%). $^1$H NMR (400 MHz, DMSO-d$^6$): δ 8.61 (d, J=8.5 Hz, 1H), 8.21 (d, J=8.6 Hz, 1H), 7.92 (d, J=8.0 Hz, 1H), 7.83 (d, J=7.3 Hz, 1H), 7.63 (t, J=7.8 Hz, 1H). ESI-MS (−): m/z 203.08 [M−H]$^-$.

Example 28

Dimethyl 8,8'-disulfanediylbis(quinoline-2-carboxylate) (15) In a 10 mL microwave tube was placed 14b (0.02 g, 0.97 mmol) and methanol (2 mL), followed by approximately 15 drops of conc. H$_2$SO$_4$. The solution was placed in a microwave reactor and heated to 90° C. with stirring for 24 min. The solution was evaporated to dryness and the crude material was taken back with CHCl$_3$ and washed with a sat. NaHCO$_3$ (3×50 mL). The crude material was dried and concentrated. Yield=0.02 g (84%). $^1$H NMR (400 MHz, CDCl$_3$): δ 8.33 (dd, J=8.7, 1.4 Hz, 1H), 8.26 (dd, J=8.5, 1.4 Hz, 1H), 7.95 (d, J=7.5 Hz, 1H), 7.68 (d, J=8.2 Hz, 1H), 7.47 (td, J=7.8, 1.5 Hz, 1H), 4.10 (s, 3H).

Example 29

8-(tert-Butylthio)quinoline-3-carboxylic acid (16a). To a solution of 8-fluoroquinoline-3-carboxylic acid (1 g, 5.2 mmol) in DMF (40 mL) was added NaH (0.5 g, 20.8 mmol) and tert-butylthiol (2.35 mL, 20.8 mmol) under nitrogen atmosphere. The mixture was stirred at 140° C. for 18 h. The solution was evaporated to dryness and the crude material was taken up in water and acidified with 6M HCl until a precipitate was formed (pH 2). The precipitate was filtered and dried under vacuum. Yield=1.47 g (100%). $^1$H NMR (400 MHz, DMSO-d$^6$): δ 9.35 (d, J=2.0 Hz, 1H), 8.96 (d, J=1.9 Hz, 1H), 8.20-8.15 (m, 1H), 8.10 (d, J=7.2 Hz, 1H), 7.67 (dd, J=8.2, 7.2 Hz, 1H), 1.30 (s, 9H). ESI-MS(+): m/z 261.97 [M+H]$^+$.

Example 30

8,8'-Disulfanediylbis(quinoline-3-carboxylic acid) (16b). A solution of 16a (0.6 g, 2.3 mmol) in conc. HCl (50 mL) was stirred at 110° C. for 12 h. The mixture was neutralized to pH 9 and washed with EtOAc (2×50 mL). The aqueous layer was then acidified to pH 2-3 and the precipitate was filtered off and dried under vacuum. The crude material was recrystallized from EtOH. The product was isolated as a disulfide dimer as evidenced by mass spectrometry. Yield=0.18 g (38%). $^1$H NMR (400 MHz, DMSO-d$^6$): δ 9.38 (d, J=1.6 Hz, 1H), 9.02 (d, J=1.6 Hz, 1H), 8.04 (d, J=8.0 Hz, 1H), 7.87 (d, J=8.0 Hz, 1H), 7.62 (t, J=7.8 Hz, 1H). ESI-MS(+): m/z 409.01 [M+H]$^+$.

Example 31

Dimethyl 8,8'-disulfanediylbis(quinoline-3-carboxylate) (17) In a 10 mL microwave tube was placed 16b (0.020 g, 0.97 mmol) and methanol (2 mL) followed by approximately 15 drops of conc. H$_2$SO$_4$. The solution was placed in a microwave reactor and heated to 90° C. with stirring for 20 min. The solution was evaporated to dryness and the crude material was taken back with CHCl$_3$ and washed with a sat. solution of NaHCO$_3$ (3×50 mL). The crude material was then dried, evaporated to dryness and recrystallized from EtOH. Yield=0.004 g (19%). $^1$H NMR (400 MHz, DMSO-d$^6$): δ 9.41 (d, J=2.0 Hz, 1H), 9.10 (d, J=2.0 Hz, 1H), 8.08 (d, J=8.1 Hz, 1H), 7.89 (d, J=7.5 Hz, 1H), 7.69-7.59 (m, 1H), 3.98 (s, 3H).

Example 32

8-Fluoroquinoline-4-carboxylic acid (18b). To a solution of 7-fluoroisatin (0.5 g, 3.03 mmol) in water (10 mL) in a 35 mL microwave tube was added 5M NaOH (2.52 mL, 15.1 mmol) and sodium pyruvate (0.4 g, 3.66 mmol). The mixture was placed in a microwave reactor and heated to 110° C. with stirring for 10 min. After cooling, the suspension containing the dicarboxylic acid derivative was acidified to pH 2 and the dark solid was filtered off to afford 18a. A portion of 18a (0.17 g) was then placed in a 10 mL microwave tube and H$_2$O (2 mL) was added. The suspension was placed in a microwave reactor and heated to 170° C. (or 280 psi) with stirring for 5 min. The brown solid was then filtered off and dried under vacuum. Yield=60% over 2 steps. $^1$H NMR (400 MHz, DMSO-d$^6$): δ 9.07 (d, J=4.1 Hz, 1H), 8.48 (d, J=7.4 Hz, 1H), 8.00 (d, J=4.1 Hz, 1H), 7.73-7.62 (m, 2H). ESI-MS(+): m/z 192.27 [M+H]$^+$.

Example 33

8-(tert-Butylthio)quinoline-4-carboxylic acid (18c). To a solution of 18b (0.3 g, 1.57 mmol) in DMF (30 mL) was added NaH (0.15 g, 6.3 mmol) and tert-butylthiol (707 µL, 36.3 mmol) under nitrogen atmosphere. The mixture was stirred at 140° C. for 18 h. The solution was evaporated to dryness and the crude material was taken up in water and acidified until a precipitate formed (pH 2). The precipitate was filtered and discarded (side product) and the filtrate was extracted with EtOAc (3×50 mL), dried and concentrated. H$_2$O was added to the crude material and a yellow solid precipitated out of the solution and was collected by filtration. Yield=0.2 g (49% yield). $^1$H NMR (400 MHz, DMSO-d$^6$): δ 9.07 (d, J=4.1 Hz, 1H), 8.60 (d, J=8.6 Hz, 1H), 8.05 (d, J=7.1 Hz, 1H), 7.90 (d, J=4.3 Hz, 2H), 7.68 (t, J=7.9 Hz, 2H), 1.30 (s, 9H). ESI-MS(+): m/z 261.93 [M+H]$^+$.

Example 34

8,8'-Disulfanediylbis(quinoline-4-carboxylic acid) (18d). A solution of 18c (0.2 g, 0.76 mmol) in conc. HCl (18 mL) was stirred at 110° C. for 12 h. The crude material was neutralized to pH 9 and washed EtOAc (3×10 mL). The aqueous layer was then acidified to pH 2-3 and the precipitate was filtered off and dried under vacuum. The product was isolated as a disulfide dimer as evidenced by mass spectrometry. Yield=0.09 g (58% yield). $^1$H NMR (400 MHz, DMSO-d$^6$): δ 9.13 (d, J=4.5 Hz, 1H), 8.49 (d, J=8.5 Hz, 1H), 8.05 (d, J=4.4 Hz, 1H), 7.78 (d, J=7.5 Hz, 1H), 7.61 (t, J=8.0 Hz, 1H). ESI-MS(−): m/z 406.96 [M−H]$^-$.

Example 35

Dimethyl 8,8'-disulfanediylbis(quinoline-4-carboxylate) (19) In a 10 mL microwave tube was placed 18d (0.02 g, 0.97 mmol) and MeOH (2 mL), followed by approximately 15 drops of conc. H$_2$SO$_4$. The solution was placed in a microwave reactor and heated to 90° C. with stirring for 20 min. The solution was evaporated to dryness and the crude material was taken back with CHCl$_3$ and washed with a sat. solution of NaHCO$_3$ (3×50 mL). The crude material was dried, concentrated and recrystallized from EtOH. Yield=0.02 g (100% yield). $^1$H NMR (400 MHz, CDCl$_3$): δ 8.99 (dd, J=4.2, 1.7, 0.8 Hz, 1H), 8.12 (dd, J=8.3, 1.7, 0.8 Hz, 1H), 7.89 (d, J=8.8 Hz, 1H), 7.53 (dd, J=8.3, 4.2 Hz, 1H), 7.27 (d, J=1.8 Hz, 1H), 4.04 (d, J=0.8 Hz, 3H). ESI-MS(+): m/z 437.02 [M+H]$^+$.

Example 36

8,8'-Disulfanediylbis(N-(thiophen-2-ylmethyl)quinoline-2-carboxamide) (20). To a solution of 14b (0.05 g, 0.24 mmol) in dry CH$_2$Cl$_2$ (2 mL) was added oxalyl chloride (320 µL, 2.90 mmol) and 12 drops of dry DMF under nitrogen atmosphere. The solution was stirred at room temperature for 2 h. The solution was evaporated to dryness to remove the excess of oxalyl chloride. The acyl chloride solution was then added to a solution of 2-thiophenemethylamine (300 µL, 2.9 mmol) in dry CH$_2$Cl$_2$ (6 mL) under nitrogen atmosphere and stirred at room temperature for 18 h. The solution was washed with 1M HCl to remove excess of amine, dried and concentrated under reduced pressure. The crude material was purified via silica gel column chromatography using a gradient of 0 to 100% EtOAc in hexanes. Yield=0.06 g (79%). $^1$H NMR (400 MHz, CDCl$_3$): δ 8.59 (t, J=6.2 Hz, 1H, NH), 8.45-8.40 (m, 1H), 8.39-8.32 (m, 1H), 7.87 (d, J=7.6 Hz, 1H), 7.72-7.66 (m, 1H), 7.51-7.41 (m, 1H), 7.25-7.23 (m, 1H), 7.15-7.11 (m, 1H), 7.03-6.95 (m, 1H), 4.95 (d, J=5.8 Hz, 2H). ESI-MS(+): m/z 598.93 [M+H], 621.03 [M+Na]$^+$.

Example 37

8,8'-Disulfanediylbis(N-benzylquinoline-2-carboxamide) (21) To a solution of 14b (0.05 g, 0.24 mmol) in dry CH$_2$Cl$_2$ (2 mL) was added oxalyl chloride (42 μL, 0.48 mmol) and 5 drops of dry DMF under nitrogen atmosphere. The solution was stirred at room temperature for 2 h. The solution was evaporated to dryness to remove the excess of oxalyl. The acyl chloride solution was then added to a solution of benzylamine (319 μL, 2.9 mmol) in dry CH$_2$Cl$_2$ (5 mL) under nitrogen atmosphere and the mixture was stirred at room temperature for 18 h. The solution was washed with 1M HCl to remove excess of benzylamine, dried and concentrated under reduced pressure. The crude material was purified via silica gel column using a gradient of 0 to 100% EtOAc in hexanes. Yield=0.05 g (74%). $^1$H NMR (400 MHz, CDCl$_3$): δ 8.60 (t, J=6.2 Hz, 1H, NH), 8.43 (d, J=8.5 Hz, 1H), 8.36 (d, J=8.6 Hz, 1H), 7.86 (dd, J=7.5, 1.2 Hz, 1H), 7.69 (dd, J=8.2, 1.2 Hz, 1H), 7.49-7.43 (m, 3H), 7.40-7.34 (m, 2H), 7.30 (d, J=7.2 Hz, 1H), 4.80 (d, J=6.2 Hz, 2H). ESI-MS(+): m/z 587.08 [M+H]$^+$, 609.11 [M+Na]$^+$.

Example 38

(Compound 1) 8,8'-Disulfanediylbis(quinoline-3-carboxamide). To a solution of 16b (0.05 g, 0.24 mmol) in DMF (5 mL) was added CDI (0.06 g, 0.37 mmol) and stirred at room temperature for ~15 min under nitrogen atmosphere. To this was added ammonium hydroxide (0.305 g, 2.44 mmol) and allowed to stir for 1 h. The resulting solution was concentrated under reduced pressure, then purified via reverse-phase chromatography eluting using a gradient of 0 to 100% acetonitrile in H$_2$O. Yield=0.016 g (32%). $^1$H NMR (400 MHz, DMSO-d$^6$): δ 9.37 (d, J=2.0 Hz, 1H), 8.91 (d, J=2.0 Hz, 1H), 8.38 (b, 1H), 7.94 (d, J=8.4 Hz, 1H), 7.82 (m, 2H), 7.61 (t, J=8.0 Hz, 1H). HRMS calcd for [C$_{20}$H$_{15}$N$_4$O$_2$S$_2$]$^+$: 407.0631; Found: 407.0637.

Example 39

(Compound 2) 8,8'-Disulfanediylbis(N-methylquinoline-3-carboxamide). To a solution of 16b (0.05 g, 0.24 mmol) in DMF (5 mL) was added hydroxybenzotriazole (HOBT, 0.06 g, 0.37 mmol) and EDC (-Ethyl-3-(3-dimethylaminopropyl) carbodiimide, 0.07 g, 0.37 mmol) and stirred at room temperature for ~15 min under nitrogen atmosphere. To this was added methylamine (THF solution, 0.49 mmol) and allowed to stir for 1 h. The resulting solution was concentrated under reduced pressure, then purified via reverse-phase chromatography using a gradient of 0 to 100% acetonitrile in H$_2$O. Yield=0.018 g (34%). $^1$H NMR (400 MHz, DMSO-d$^6$): δ 9.35 (s, 1H), 8.89 (m, 2H), 7.95 (d, J=8.0 Hz, 1H), 7.83 (d, J=8.0 Hz, 1H), 7.60 (t, J=8.0 Hz, 1H), 2.84 (s, 3H). HRMS calcd for [C$_{22}$H$_{19}$N$_4$O$_2$S$_2$]$^+$: 435.0944; Found: 435.0947.

Example 40

(Compound 3) Dimethyl 2,2'-((8,8'-disulfanediylbis(quinoline-8,3-diyl-3-carbonyl))bis(azanediyl))diacetate. To a solution of 16b (0.04 mg, 0.17 mmol) in DMF (4 mL) was added HATU (1-[Bis(dimethylamino)methylene]-1H-1,2,3-triazolo[4,5-b]pyridinium-3-oxidhexafluorophosphate, 0.08 g, 0.21 mmol), HOBT (0.03 g, 0.21 mmol), Et$_3$N (73 μL, 0.52 mmol) and methyl 2-aminoacetate (24 mg, 0.19 mmol) and allowed to stir at room temperature for 1 h. The resulting solution was concentrated under reduced pressure, the crude material was then dissolved in CH$_2$Cl$_2$ and washed with 1M HCl solution. The product, which precipitated out of the organic layer, was recrystallized from MeOH. Yield=0.005 g (11%). $^1$H NMR (400 MHz, DMSO-d$^6$): δ 9.42 (t, J=5.9 Hz, 1H, NH), 9.37 (s, 1H), 8.93 (s, 1H), 7.97 (d, J=8.2 Hz, 1H), 7.85 (d, J=7.5 Hz, 1H), 7.62 (t, J=7.7 Hz, 1H), 4.13 (d, J=5.7 Hz, 2H), 3.68 (s, 3H).

Example 41

Procedure for the Amide Coupling (Method A). To a solution of 16b (0.2 g, 0.98 mmol) in DMF (10 mL) was added CDI (0.24 g, 1.46 mmol) and stirred at room temperature for ~15 min under nitrogen atmosphere. To this solution was added the corresponding amine (0.146 mmol) and the solution was stirred for an additional 12 h. The resulting solution was concentrated under reduced pressure, then purified via reverse-phase chromatography using a gradient of 0 to 100% acetonitrile in H$_2$O.

Example 42

Procedure for the Amide Coupling (Method B). To a solution of 16b (0.2 g, 0.98 mmol) in DMF (10 mL) was added HATU (0.56 g, 1.46 mmol) and Et$_3$N (0.204 μL, 1.46 mmol) and the mixture was stirred at 60° C. for ~15 min under nitrogen atmosphere. To this was added the corresponding amine (0.146 mmol) and the solution was stirred for an additional 12 h. The resulting solution was concentrated under reduced pressure, then purified via reverse-phase chromatography eluting using a gradient of 0 to 100% acetonitrile in H$_2$O.

Example 43

Compound 4. 8,8'-Disulfanediylbis(N-(oxazol-2-yl)quinoline-3-carboxamide). Product afforded via Method B. Yield=0.13 g (48%). $^1$H NMR (400 MHz, DMSO-d$^6$): δ 9.47 (s, 1H), 9.06 (d, J=1.6 Hz, 1H), 8.01 (d, J=8.0 Hz, 1H), 7.93 (s, 1H), 7.87 (d, J=8.0 Hz, 1H), 7.64 (t, J=8.0 Hz, 1H), 7.25 (s, 1H).

Example 44

Compound 5. 8,8'-Disulfanediylbis(N-(thiazol-2-yl)quinoline-3-carboxamide). Product afforded via Method B. Reaction mixture was heated at 60° C. for 12 h. To the reaction solution was added H$_2$O, which resulted in formation of a precipitate, which was isolated through filtration to afford product. Yield=0.12 g (43%). $^1$H NMR (400 MHz, DMSO-d$^6$): δ 9.51 (s, 1H), 9.15 (s, 1H), 7.98 (d, J=8.0 Hz, 1H), 7.88 (d, J=8.0 Hz, 1H), 7.64-7.59 (m, 2H), 7.32 (d, J=2.4 Hz, 1H). HRMS calcd for [C$_{26}$H$_{16}$N$_6$O$_2$S$_4$Na]$^+$: 595.0110; Found: 595.0103.

Example 45

Compound 6. 8,8'-Disulfanediylbis(N-((tetrahydrofuran-2-yl)methyl)quinoline-3-carboxamide). Product afforded via Method A. Yield=0.14 g (51%). $^1$H NMR (400 MHz, DMSO-d$_6$): δ 9.43 (d, J=2 Hz, 1H), 8.88 (d, J=2 Hz, 1H), 7.94-7.90 (m, 3H), 7.60 (t, J=8 Hz, 1H), 4.13-3.47 (m, 5H), 2.09-1.67 (m, 4H). HRMS calcd for [C$_{30}$H$_{31}$N$_4$O$_4$S$_2$]$^+$: 575.1781; Found: 575.1780.

Example 46

Compound 7. 8,8'-Disulfanediylbis(N-(furan-2-ylmethyl)quinoline-3-carboxamide). Product afforded via Method A. Yield=0.084 g (30%). $^1$H NMR (400 MHz, DMSO-d$_6$): δ 9.46 (d, J=2.4 Hz, 1H), 8.99 (d, J=2.4 Hz, 1H), 8.50 (br, 1H), 8.35 (dd, J=7.2, 1.2 Hz, 1H), 8.28 (dd, J=7.2, 1.2 Hz, 1H), 7.84 (t, J=7.6 Hz, 1H), 7.50 (dd, J=1.6, 0.8 Hz, 1H), 6.40 (m, 2H), 4.67 (d, J=5.6 Hz, 2H). HRMS calcd for [C$_{30}$H$_{22}$N$_4$O$_4$S$_2$Na]$^+$: 589.0975; Found: 589.0972.

Example 47

Compound 8. 8,8'-Disulfanediylbis(N-(thiophen-2-ylmethyl)quinoline-3-carboxamide). Product afforded via Method A. Yield=0.13 g (44%). $^1$H NMR (400 MHz, DMSO-d$_6$): δ 9.58 (t, J=5.6 Hz, 1H), 9.37 (d, J=2.4 Hz, 1H), 8.91 (d, J=2.4 Hz, 1H), 7.96 (d, J=8 Hz, 1H), 7.84 (d, J=8 Hz, 1H), 7.62 (t, J=8 Hz, 1H), 7.42 (d, J=6 Hz, 1H), 7.09-6.97 (m, 2H), 4.73 (d, J=5.6 Hz, 2H). HRMS calcd for [C$_{30}$H$_{23}$N$_4$O$_2$S$_4$]$^+$: 599.0698; Found: 599.0701.

Example 48

Compound 9. 8,8'-Disulfanediylbis(N-(thiazol-2-ylmethyl)quinoline-3-carboxamide). Product afforded via Method A. To the reaction solution was added H$_2$O, which resulted in formation of a precipitate, which was isolated through filtration to afford product. Yield=0.035 g (12%). $^1$H NMR (400 MHz, DMSO-d$_6$): δ 9.83 (t, J=5.6 Hz, 1H), 9.40 (d, J=2 Hz, 1H), 8.95 (d, J=2 Hz, 1H), 7.97 (d, J=8 Hz, 1H), 7.86 (d, J=8 Hz, 1H), 7.76 (d, J=3.2 Hz, 1H), 7.66 (d, J=3.2 Hz, 1H), 7.63 (t, J=8 Hz, 1H), 4.86 (d, J=6 Hz, 2H). HRMS calcd for [C$_{28}$H$_{21}$N$_6$O$_2$S$_4$]$^+$: 601.0603; Found: 601.0600.

Example 49

Compound 10. 8,8'-Disulfanediylbis(N-(2-(furan-2-yl)ethyl)quinoline-3-carboxamide). Product afforded via Method A. The reaction solution was concentrated and diluted with diethylether, which resulted in formation of a precipitate. The precipitate was isolated through filtration, then purified via reverse-phase chromatography eluting H$_2$O/ACN (0-100%). Yield=0.065 g (22%). $^1$H NMR (400 MHz, DMSO-d$_6$): δ 9.32 (d, J=2 Hz, 1H), 9.04 (t, J=5.2 Hz, 1H), 8.84 (d, J=2 Hz, 1H), 7.94 (d, J=8 Hz, 1H), 7.83 (d, J=8 Hz, 1H), 7.61-7.54 (m, 2H), 6.36 (t, J=2.8 Hz, 1H), 6.21 (d, J=2.8 Hz, 1H), 3.62 (q, J=6 Hz, 2H), 2.96 (q, J=7.2 Hz, 2H). HRMS calcd for [C$_{32}$H$_{26}$N$_4$O$_4$S$_2$Na]$^+$: 617.1288; Found: 617.1283

Example 50

Compound 11. 8,8'-Disulfanediylbis(N-(2-(thiophen-2-yl)ethyl)quinoline-3-carboxamide). Product afforded via Method A. To the resulting solution was added H$_2$O, which caused formation of a precipitate. The precipitate was isolated through filtration, then purified via reverse-phase chromatography eluting H$_2$O/ACN (0-100%). Yield=0.075 g (24%). $^1$H NMR (400 MHz, DMSO-d$_6$): δ 9.35 (s, 1H), 9.10 (t, J=5.2 Hz, 1H), 8.87 (s, 1H), 7.95 (d, J=6.4 Hz, 1H), 7.84 (d, J=6.4 Hz, 1H), 7.62 (t, J=5.6 Hz, 1H), 7.34-6.96 (m, 3H), 3.60 (t, J=6 Hz, 2H), 3.14 (t, J=6 Hz, 2H). HRMS calcd for [C$_{32}$H$_{27}$N$_4$O$_2$S$_4$]$^+$: 627.1011; Found: 627.1013.

Example 51

Compound 12. 8,8'-Disulfanediylbis(N-(2-(thiazol-2-yl)ethyl)quinoline-3-carboxamide). Product afforded via Method A. To the resulting solution was added H$_2$O, which caused formation of a precipitate, which was isolated through filtration to afford product. Yield=0.18 g (57%). $^1$H NMR (400 MHz, DMSO-d$_6$): δ 9.33 (s, 1H), 9.11 (t, J=5.2 Hz, 1H), 8.86 (s, 1H), 7.95 (d, J=8 Hz, 1H), 7.84 (d, J=8 Hz, 1H), 7.74 (d, J=3.2 Hz, 1H), 7.62-7.58 (m, 2H), 3.74-3.69 (m, 2H), 3.34-3.29 (m, 2H). HRMS calcd for [C$_{30}$H$_{25}$N$_6$O$_2$S$_4$]$^+$: 629.0916; Found: 629.0913.

Example 52

Compound 13. 8,8'-Disulfanediylbis(N-(pyridin-2-ylmethyl)quinoline-3-carboxamide). Product afforded via Method B. Yield=0.06 g (21%). $^1$H NMR (400 MHz, DMSO-d$_6$): δ 9.52 (d, J=2.4 Hz, 1H), 9.07 (d, J=2.4 Hz, 1H), 8.77-8.58 (m, 2H), 8.36 (dd, J=7.2, 1.2 Hz, 1H), 8.32 (dd, J=7.2, 1.2 Hz, 1H), 7.86-7.82 (m, 2H), 7.55 (d, J=8 Hz, 1H), 7.36 (t, J=6 Hz, 3H), 4.82 (d, J=6 Hz, 2H). HRMS calcd for [C$_{32}$H$_{25}$N$_6$O$_2$S$_2$]$^+$: 589.1475; Found: 589.1478.

Example 53

Compound 14. 8,8'-Disulfanediylbis(N-(pyridin-3-ylmethyl)quinoline-3-carboxamide). Product afforded via Method B. Yield=0.11 g (38%). $^1$H NMR (400 MHz, DMSO-d$_6$): δ 9.46 (d, J=2.4 Hz, 1H), 8.98 (d, J=2.4 Hz, 1H), 8.70-8.52 (m, 2H), 8.34 (dd, J=7.2, 1.2 Hz, 1H), 8.27 (dd, J=7.2, 1.2 Hz, 1H), 7.92 (d, J=7.6 Hz, 1H), 7.83 (t, J=7.6 Hz, 1H), 7.43 (dd, J=7.6, 4.8 Hz, 1H), 4.73 (d, J=5.6 Hz, 2H). HRMS calcd for [C$_{32}$H$_{25}$N$_6$O$_2$S$_2$]$^+$: 589.1475; Found: 589.1477.

Example 54

Compound 15. 8,8'-Disulfanediylbis(N-(pyridin-4-ylmethyl)quinoline-3-carboxamide). Product afforded via Method B. Yield=0.06 g (21%). $^1$H NMR (400 MHz, DMSO-d$_6$): δ 9.88 (t, J=5.6 Hz, 1H), 9.46 (d, J=2.4 Hz, 1H), 9.03 (d, J=2.4 Hz, 1H), 8.84-8.74 (m, 2H), 7.99 (d, J=8 Hz, 1H), 7.92-7.91 (m, 2H), 7.87 (d, J=8 Hz, 1H), 7.65 (t, J=8 Hz, 1H), 4.80 (d, J=5.6 Hz, 2H). HRMS calcd for [C$_{32}$H$_{26}$N$_6$O$_2$S$_2$]$^+$: 589.1475; Found: 589.1477.

Example 55

Compound 16. 8,8'-Disulfanediylbis(N-benzylquinoline-3-carboxamide). Product afforded via Method B. The resulting solution was concentrated and the crude material was dissolved in CH$_2$Cl$_2$. The product, which precipitated out of the organic layer, was collected by filtration. Yield=0.03 g (42%). $^1$H NMR (400 MHz, DMSO-d$^6$): δ 9.49 (t, J=5.9 Hz, 1H), 9.41 (d, J=2.1 Hz, 1H), 8.95 (d, J=2.2 Hz, 1H), 7.94 (s, 1H), 7.86-7.81 (m, 1H), 7.61 (t, J=7.8 Hz, 1H), 7.41-7.32 (m, 4H), 7.26 (t, J=7.1 Hz, 1H), 4.58 (d, J=5.8 Hz, 2H). HRMS calcd for [C$_{34}$H$_{27}$N$_4$O$_2$S$_2$]$^+$: 587.1570; Found: 587.1571.

Example 56

Compound 17. 8,8'-Disulfanediylbis(N-(4-fluorobenzyl)quinoline-3-carboxamide). Product afforded via Method A.

Yield=0.04 g (14%). $^1$H NMR (400 MHz, DMSO-d$^6$): δ 9.48 (t, J=5.6 Hz, 1H), 9.39 (d, J=1.6 Hz, 1H), 8.92 (d, J=1.6 Hz, 1H), 7.95 (d, J=8.0 Hz, 1H), 7.84 (d, J=8.0 Hz, 1H), 7.61 (t, J=8.0 Hz, 1H), 7.44-7.15 (m, 4H), 4.56 (d, J=5.6 Hz, 2H). HRMS calcd for [C$_{34}$H$_{25}$F$_2$N$_4$O$_2$S$_2$]: 623.1382; Found: 623.1384.

Example 57

Compound 18. 8,8'-Disulfanediylbis(N-(4-(trifluoromethyl)benzyl)quinoline-3-carboxamide). Product afforded via Method A. Yield=0.09 g (26%). $^1$H NMR (400 MHz, DMSO-d$^6$): δ 9.58 (t, J=5.6 Hz, 1H), 9.40 (s, 1H), 8.94 (s, 1H), 7.96 (d, J=8.0 Hz, 1H), 7.85 (d, J=8.0 Hz, 1H), 7.73 (d, J=8.0 Hz, 2H), 7.62-7.61 (m, 3H), 4.67 (d, J=5.2 Hz, 2H). ESI-MS(+): m/z 723.25 [M+H]$^+$. HRMS calcd for [C$_{36}$H$_{24}$F$_6$N$_4$O$_2$S$_2$Na]$^+$: 745.1137; Found: 745.1141

Example 58

Compound 19. 8,8'-Disulfanediylbis(N-(4-methoxybenzyl)quinoline-3-carboxamide). Product afforded via Method A. Yield=0.15 g (47%). $^1$H NMR (400 MHz, DMSO-d$^6$): δ 9.40-9.38 (m, 2H), 8.91 (d, J=1.6 Hz, 1H), 7.95 (d, J=8.0 Hz, 1H), 7.83 (d, J=8.0 Hz, 1H), 7.62 (t, J=8.0 Hz, 1H), 7.30 (d, J=8.0 Hz, 2H), 6.92 (d, J=8.0 Hz, 2H), 4.50 (d, J=5.6 Hz, 2H) 3.72 (s, 3H). HRMS calcd for [C$_{36}$H$_{30}$N$_4$O$_4$S$_2$Na]$^+$: 669.1601; Found: 669.1603.

Example 59

Compound 20. 8,8'-Disulfanediylbis(N-(benzo[d][1,3]dioxol-5-ylmethyl)quinoline-3-carboxamide). Product afforded via Method A. Yield=0.12 g (37%). $^1$H NMR (400 MHz, Acetone-d$_6$): 59.38 (s, 2H), 9.01 (s, 1H), 8.27-8.26 (m, 2H), 7.81 (d, J=7.6 Hz, 1H), 6.95 (s, 1H), 6.87-6.85 (m, 2H), 5.98 (s, 2H), 4.46 (d, J=5.6 Hz, 2H). HRMS calcd for [C$_{36}$H$_{27}$N$_4$O$_6$S$_2$]$^+$: 675.1372; Found: 675.1374.

Example 60

Compound 21. 8,8'-Disulfanediylbis(N-(4-morpholinobenzyl)quinoline-3-carboxamide). Product afforded via Method A. Yield=0.18 g (50%). $^1$H NMR (400 MHz, DMSO-d$^6$): δ 9.40-9.33 (m, 2H), 8.91 (s, 1H), 7.94 (d, J=8.0 Hz, 1H), 7.83 (d, J=8.0 Hz, 1H), 7.59 (t, J=8.0 Hz, 1H), 7.26 (d, J=8.0 Hz, 2H), 6.93 (d, J=8.0 Hz, 2H), 4.47 (d, J=5.6 Hz, 2H), 3.72 (t, J=4.8 Hz, 4H), 3.05 (t, J=4.8 Hz, 4H). HRMS calcd for [C$_{42}$H$_{40}$N$_6$O$_4$S$_2$Na]$^+$: 779.2445; Found: 779.2443.

Example 61

Compound 22. 8,8'-Disulfanediylbis(N-(2-morpholinoethyl)quinoline-3-carboxamide). Product afforded via Method A. Yield=0.07 g (24%). $^1$H NMR (400 MHz, Acetone-d$_6$): δ 9.45 (s, 1H), 8.96 (s, 1H), 8.36 (d, J=8 Hz, 1H), 8.30 (d, J=8 Hz, 1H), 7.86 (t, J=8 Hz, 1H), 3.79-3.75 (m, 6H), 3.06 (t, J=6 Hz, 2H). HRMS calcd for [C$_{32}$H$_{37}$N$_6$O$_4$S$_2$]$^+$: 633.2312; Found: 633.2316.

Example 62

Compound 23. 8,8'-disulfanediylbis(N-(thiophen-2-ylmethyl)quinoline-4-carboxamide). To a solution of 18d (0.05 g, 0.24 mmol) in dry CH2Cl2 (2 mL) was added oxalyl chloride (640 μL, 5.76 mmol) and 15 drops of dry DMF under nitrogen atmosphere. The solution was stirred at room temperature for 2 h. The solution was evaporated to dryness to remove the excess of oxalyl chloride and dry CH2Cl2 was added to the crude material (2 mL). The acyl chloride solution was added to a solution of 2-thiophenemethylamine (600 μL, 5.76 mmol) in dry CH2Cl2 (10 mL) under nitrogen atmosphere and stirred at room temperature for 2 days. The solution was washed with 1M HCl to remove excess of amine, dried and concentrated. The crude material was purified via silica gel column chromatography using a gradient of 0 to 100% EtOAc in hexanes. Yield=0.03 g (41% yield). 1H NMR (400 MHz, DMSO-d6): δ 9.47 (d, J=5.9 Hz, 1H), 9.08 (d, J=3.9 Hz, 1H), 7.93 (d, J=8.4 Hz, 1H), 7.74 (d, J=7.6 Hz, 1H), 7.67 (d, J=4.2 Hz, 1H), 7.59-7.51 (m, 1H), 7.43 (d, J=5.1 Hz, 1H), 7.07 (d, J=3.3 Hz, 1H), 6.98 (s, 1H), 4.70 (d, J=5.8 Hz, 2H).

Example 63

Compound 24. 8,8'-disulfanediylbis(N-(2-(thiophen-2-yl)ethyl)quinoline-4-carboxamide). 1H NMR (400 MHz, DMSO-d6) δ 9.08 (d, J=4 Hz, 1H), 8.95 (t, J=5.6 Hz, 1H), 7.82 (d, J=8 Hz, 1H), 7.75 (d, J=8 Hz, 1H), 7.64 (d, J=4 Hz, 1H), 7.53 (t, J=8 Hz, 1H), 7.36 (d, J=4.8 Hz, 1H), 6.98-6.95 (m, 2H), 3.62 (q, J=6.4 Hz, 2H), 3.13 (t, J=6.4 Hz, 2H). HRMS calcd for [C32H26N4O4S2Na]+: 649.0831; Found: 649.0821.

Example 64

Compound 25. 8,8'-Disulfanediylbis(N-(furan-2-ylmethyl)quinoline-4-carboxamide). To a solution of 18d (0.2 g, 0.98 mmol) in DMF (10 mL) was added carbonyldimidazole (CDI, 0.24 g, 1.46 mmol) and stirred at room temperature for ~15 min under nitrogen atmosphere. To this was added furan-2-ylmethanamine (0.146 mmol) and stirred for an additional 12 h. The resulting solution was concentrated under reduced pressure, then purified via silica gel column chromatography using a gradient of 0 to 100% EtOAc in hexanes. Yield=0.15 g (54%). 1H NMR (400 MHz, DMSO-d6): δ 9.33 (t, J=5.6 Hz, 1H), 9.08 (d, J=4.4 Hz, 1H), 7.92 (d, J=8.4 Hz, 1H), 7.76 (d, J=7.6 Hz, 1H), 7.69-7.61 (m, 2H), 7.57 (t, J=8.0 Hz, 1H), 6.43-6.36 (m, 2H), 4.55 (d, J=5.6 Hz, 2H).

Example 65

Compound 26. 8,8'-disulfanediylbis(N-(2-(furan-2-yl)ethyl)quinoline-4-carboxamide).(26) 1H NMR (400 MHz, DMSO-d6) δ 9.07 (d, J=4.4 Hz, 1H), 8.92 (t, J=5.6 Hz, 1H), 7.85 (d, J=8 Hz, 1H), 7.74 (d, J=8 Hz, 1H), 7.62-7.50 (m, 3H), 6.37 (d, J=1.6 Hz, 1H), 6.21 (d, J=1.6 Hz, 1H), 3.59 (q, J=6.4 Hz, 2H), 2.94 (t, J=6.4 Hz, 2H). HRMS calcd for [C32H26N4O4S2Na]+: 617.1288; Found: 617.1286.

Example 66

Synthetic Scheme for Compounds 27, 28, 29, and 30

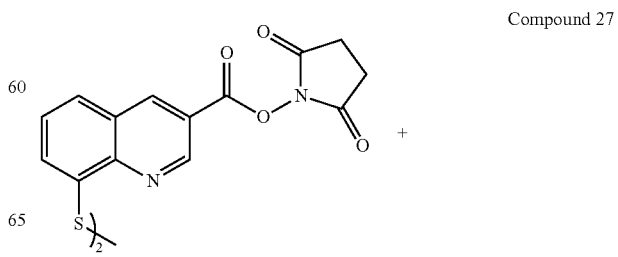

Compound 27

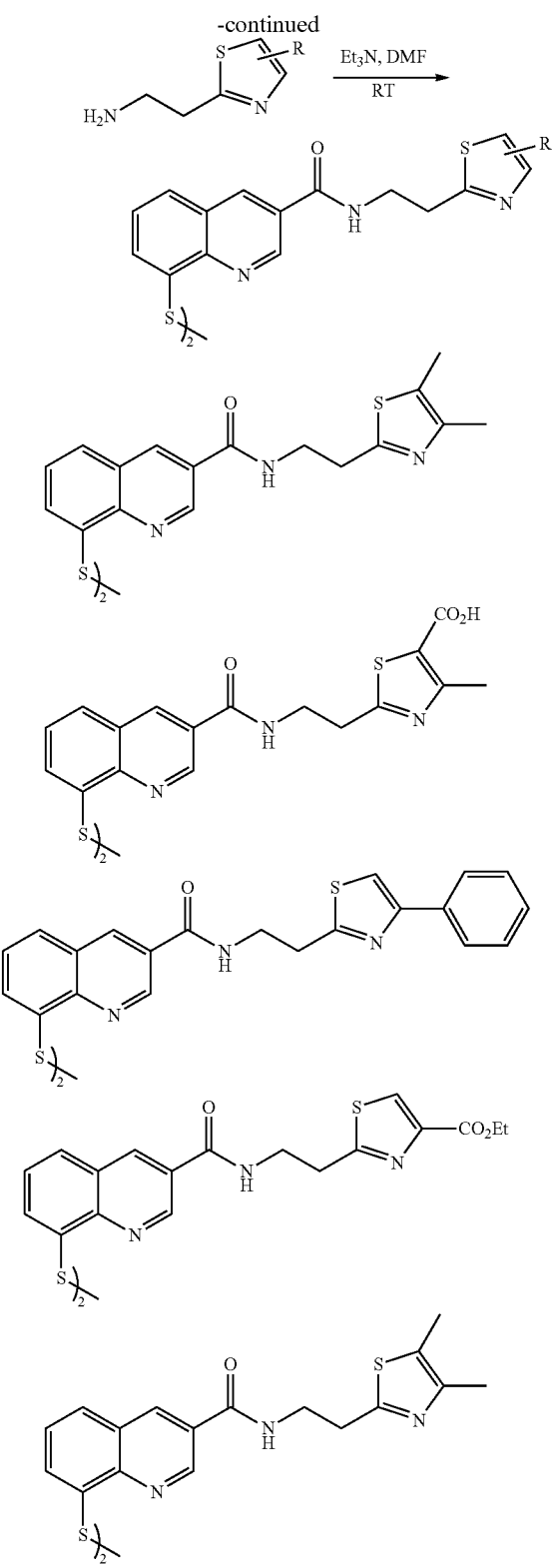

Compound 27

Example 67

Compound 27. To a solution of the NHS ester (30 mg, 0.099 mmol) in DMF (2.0 mL) were added Et$_3$N (0.041 mL, 0.298 mmol) and the amine (19 mg, 0.099 mmol) at room temperature. After stirring for 12 h, the reaction was mixture was concentrated. The resulting residue was purified via silica gel column chromatography (dichloromethane/methanol: 0%~10%) to give the desired product (30 mg, 88%) as a white solid. $^1$H NMR (400 MHz, CDCl$_3$): δ 9.34 (d, J=2.0 Hz, 1H), 8.68 (d, J=2.0 Hz, 1H), 8.02 (t, J=5.4 Hz, 1H), 7.93 (d, J=7.6 Hz, 1H), 7.68 (d, J=8.0 Hz, 1H), 7.44 (dd, J=8.0, 7.6 Hz, 1H), 3.94 (q, J=6.0 Hz, 2H), 3.26 (t, J=6.0 Hz, 2H), 2.35 (s, 3H), 2.32 (s, 3H). $^{13}$C NMR (125 MHz, CDCl$_3$): δ 165.1, 163.6, 147.4, 146.7, 136.0, 135.5, 127.8, 127.7, 127.2, 126.3, 126.2, 39.1, 31.8, 14.7, 11.3. ESI-MS Calcd for C$_{34}$H$_{33}$N$_6$O$_2$S$_4$ [M+H]$^+$: 685.15, Found: 685.38.

Compound 28

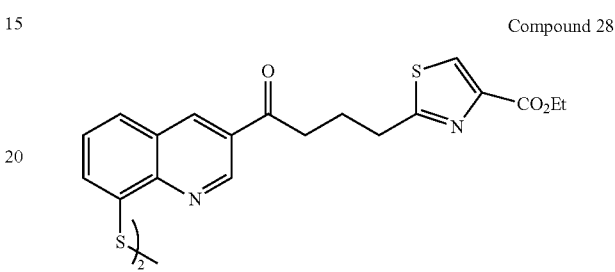

Example 68

Compound 28. To a solution of the NHS ester (30 mg, 0.099 mmol) in DMF (2.0 mL) were added Et$_3$N (0.041 mL, 0.298 mmol) and the amine (20 mg, 0.099 mmol) at room temperature. After stirring for 12 h, the reaction was mixture was concentrated. The resulting residue was recrystalized from MeOH and the desired product was obtained (31 mg, 81%) as a white solid. $^1$H NMR (400 MHz, DMSO): δ 9.32 (d, J=2.0 Hz, 1H), 9.10 (t, J=4.8 Hz, 1H), 8.85 (d, J=2.0 Hz, 1H), 8.41 (s, 1H), 7.95 (d, J=8.0 Hz, 1H), 7.83 (d, J=7.2 Hz, 1H), 7.60 (t, J=7.8 Hz, 1H), 4.28 (q, J=7.2 Hz, 2H), 3.73 (q, J=6.0 Hz, 2H), 3.15 (d, J=5.2 Hz, 2H), 1.27 (t, J=7.2 Hz, 3H). $^{13}$C NMR (125 MHz, DMSO): δ 168.8, 165.2, 161.3, 148.7, 146.2, 146.1, 136.5, 129.7, 128.4, 127.4, 127.3, 61.2, 49.1, 32.9, 14.7. ESI-MS Calcd for Chemical Formula: C$_{36}$H$_{32}$N$_6$NaO$_6$S$_4$ [M+H]$^+$: 795.12, Found: 795.27.

Compound 29

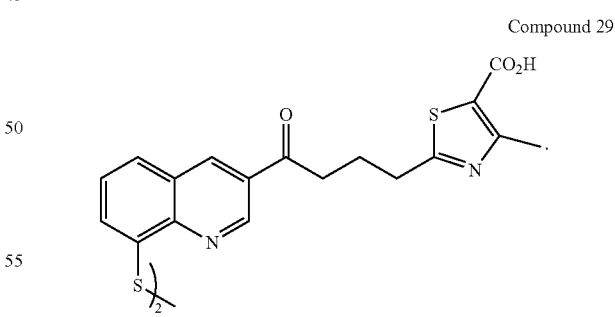

Example 69

Compound 29. To a solution of the NHS ester (30 mg, 0.099 mmol) in DMF (2.0 mL) were added Et$_3$N (0.041 mL, 0.298 mmol) and the amine (22 mg, 0.099 mmol) at room temperature. After stirring for 12 h, the reaction was mixture was concentrated. The resulting residue was recrystalized from MeOH and the desired product was obtained (32 mg, 86%) as a white solid. $^1$H NMR (400 MHz, DMSO): δ 9.33 (s, 1H), 9.11 (s, 1H), 8.66 (s, 1H), 7.94 (d, J=8.0 Hz, 1H), 7.84 (d, J=7.6 Hz, 1H), 7.61 (t, J=7.6 Hz, 1H), 3.80-3.63 (m, 2H), 3.30-3.23 (m, 2H), 2.59 (s, 3H). $^{13}$C NMR (125 MHz, DMSO): δ 170.5, 165.2, 163.5, 158.6, 148.7, 146.1, 136.5, 134.7, 128.5, 128.3, 127.4, 127.3, 126.1, 123.4, 46.0, 33.2, 17.4. ESI-MS Calcd for $C_{34}H_{27}N_6O_6S_4$ [M−H]$^-$: 743.09, Found: 743.04.

Compound 30

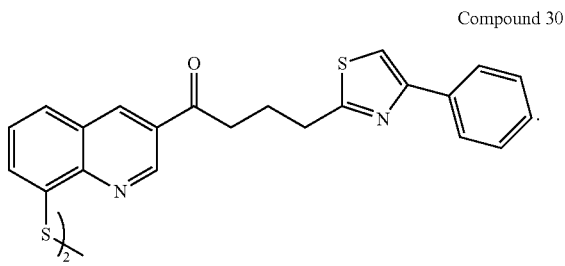 [SMILES: CSc1cccc2cc(C(=O)CCCc3nc(-c4ccccc4)cs3)cnc12]

Example 70

Compound 30. To a solution of the NHS ester (30 mg, 0.099 mmol) in DMF (2.0 mL) were added Et$_3$N (0.041 mL, 0.298 mmol) and the amine (20 mg, 0.099 mmol) at room temperature. After stirring for 12 h, the reaction was mixture was concentrated. The resulting residue was recrystalized from MeOH and the desired product was obtained (32 mg, 82%) as a white solid. $^1$H NMR (400 MHz, DMSO): δ 9.34 (d, J=2.0 Hz, 1H), 9.13 (t, J=5.6 Hz, 1H), 8.87 (d, J=2.4 Hz, 1H), 7.98 (s, 1H), 7.97-7.90 (m, 3H), 7.83 (dd, J=7.8, 1.0 Hz, 1H), 7.60 (t, J=8.0 Hz, 1H), 7.44-7.37 (m, 2H), 7.35-7.28 (m, 1H), 3.78 (q, J=6.4 Hz, 2H), 3.37 (t, J=6.8 Hz, 2H), 2.35 (s, 3H), 2.32 (s, 3H). $^{13}$C NMR (125 MHz, DMSO): δ 167.9, 165.2, 154.3, 148.7, 146.1, 136.5, 134.7, 134.6, 129.2, 128.5, 128.4, 127.4, 127.3, 126.4, 114.5, 55.4, 33.0. ESI-MS Calcd for $C_{42}H_{32}N_6NaO_2S_4$ [M+Na]$^+$: 803.14, Found: 803.17.

Example 71

Synthetic Scheme for Compound 31

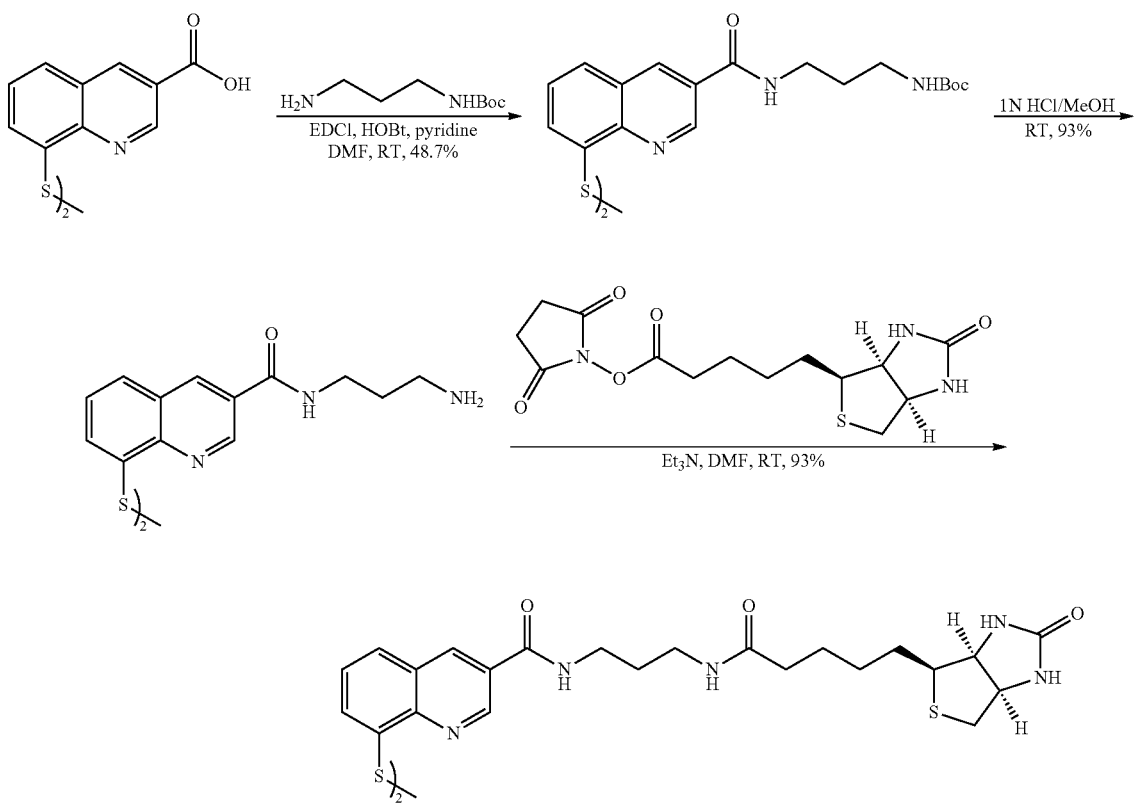

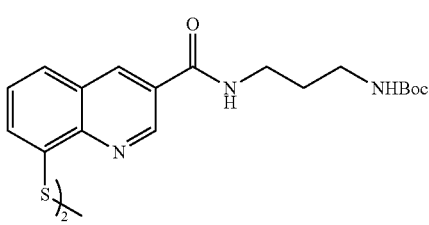

Example 72

Compound 31. To a solution of 8-((4-methoxybenzyl)thio)quinoline-3-carboxylic acid (100 mg, 0.49 mmol) in DMF (5.0 mL) was added tert-butyl (3-aminopropyl)carbamate (102 mg, 0.594 mmol), pyridine (196 uL, 1.96 mmol), HOBt (132 mg, 0.98 mmol) and EDCI (188 mg, 0.98 mmol) at room temperature. After stirring for 2 h, the reaction was monitored by TLC which indicated the complete consumption of the starting material. The reaction mixture was concentrated, the resulting residue was purified via silica gel column chromatography (dichloromethane/ethyl acetate: 30%~70%) to give the desired product (85.7 mg, 49%) as a white solid. $^1$H NMR (400 MHz, DMSO): δ 9.34 (d, J=2.4 Hz, 1H), 8.91-8.82 (m, 2H), 7.94 (dd, J=8.4, 1.2 Hz, 1H), 7.82 (dd, J=7.6 Hz, J=1.2 Hz, 1H), 7.60 (t, J=8.0 Hz, 1H), 6.86 (t, J=1.2 Hz, 1H), 3.38-3.32 (m, 2H), 3.10-2.95 (m, 2H), 1.76-1.67 (m, 2H), 1.37 (s, 9H). $^{13}$C NMR (125 MHz, DMSO): δ 164.9, 156.1, 148.8, 146.1, 136.3, 134.7, 128.6, 128.3, 127.4, 127.23, 126.0, 78.0, 38.2, 37.7, 29.9, 28.7. ESI-MS Calcd for $C_{36}H_{46}N_6O_6S_2$ [M+H]$^+$: 721.28, Found: 721.19.

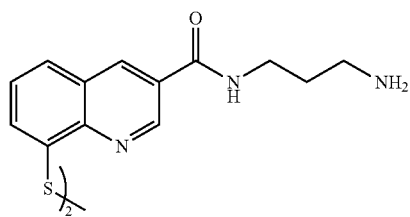 [SMILES: CSc1cccc2cc(C(=O)NCCCN)cnc12]

A suspension of the Boc protected amine (30 mg, 0.0835 mmol) in MeOH (4.0 mL) was added 1 N HCl (1.0 mL) and stirred at 50° C. After stirring for 12 h. the suspension became clear and TLC showed that the SM was completely comsumed. Then the reaction mixture was diluted with MeOH and concentrated. The resulting residue (28.5 mg, 93%) was characterized by NMR. $^1$H NMR (400 MHz, CD$_3$OD): δ 9.63 (s, 1H), 9.55 (s, 1H), 8.42 (d, J=8.4 Hz, 1H), 8.03 (d, J=7.2 Hz, 1H), 3.70-3.58 (m, 2H), 3.17-3.09 (m, 2H), 2.15-2.05 (m, 2H). $^{13}$C NMR (100 MHz, CD$_3$OD): δ 163.7, 146.2, 144.5, 140.0, 139.9, 132.0, 129.7, 129.3, 128.8, 128.6, 37.1, 36.7, 27.2. ESI-MS Calcd for $C_{26}H_{29}N_6O_2S_2$ [M+H]$^+$: 521.18, Found: 521.22.

Compound 31

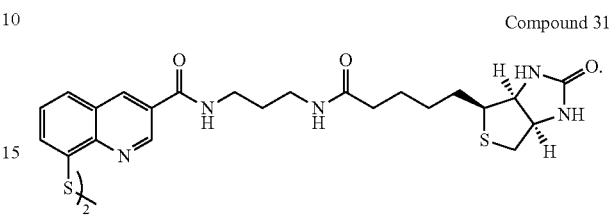

To a solution of the free amine (20 mg, 0.077 mmol) in DMF were added Et$_3$N (0.107 mL, 0.77 mmol) and the Biotin NHS ester (26 mg, 0.077 mmol) at room temperature. After stirring for 12 h, the reaction mixture was concentrated. The resulting residue was recrystalized in MeOH and the desired product was obtained (35 mg, 93%) as a white solid. $^1$H NMR (400 MHz, CDCl$_3$): δ 9.35 (d, J=2.4 Hz, 1H), 8.93-8.80 (m, 2H), 7.94 (dd, J=8.8, 1.2 Hz, 1H), 7.88-7.80 (m, 2H), 7.60 (t, J=7.6 Hz, 1H), 6.41 (s, 1H), 6.34 (s, 1H), 4.33-4.25 (m, 1H), 4.15-4.07 (m, 1H), 3.41-3.31 (m, 2H), 3.20-3.04 (m, 3H), 2.79 (dd, J=12.4, 5.0 Hz, 1H), 2.56 (d, J=12.4 Hz, 1H), 2.12-2.03 (m, 2H), 1.80-1.20 (m, 8H). $^{13}$C NMR (125 MHz, CDCl$_3$): δ 172.5, 164.9, 163.2, 148.8, 146.1, 136.3, 134.7, 128.6, 128.4, 127.4, 127.3, 126.09, 61.5, 59.6, 55.9, 37.8, 36.8, 35.7, 29.7, 28.7, 28.5, 25.8. ESI-MS Calcd for $C_{46}H_{57}N_{10}O_6S_4$ [M+H]$^+$: 973.33, Found: 973.35.

Example 73

Synthetic Scheme for Compound 32

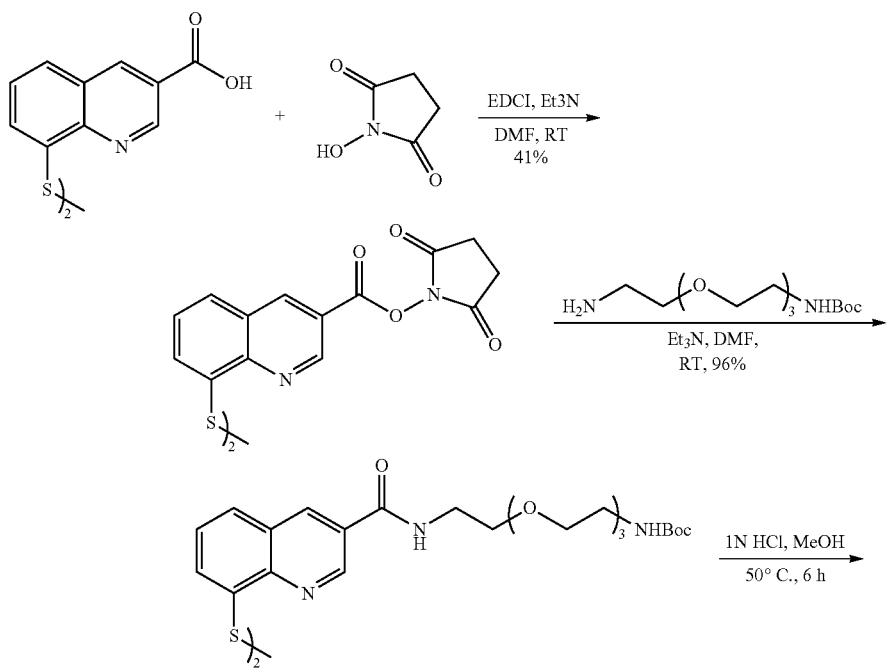

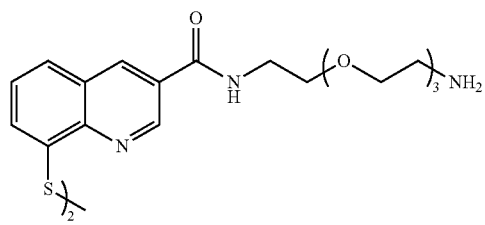 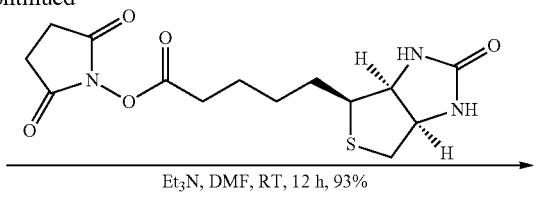

Et₃N, DMF, RT, 12 h, 93%

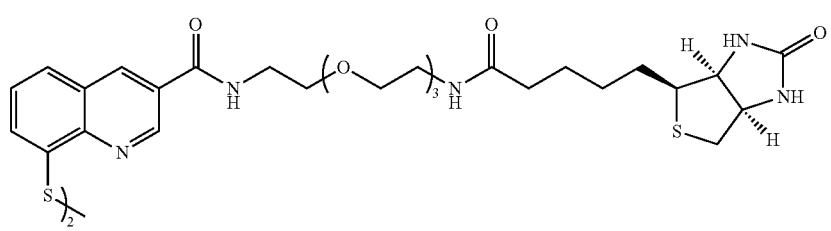

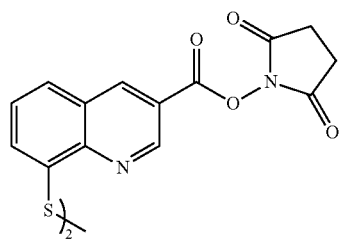

Example 74

Synthesis of Compound 32. To a solution of 8-((4-methoxybenzyl)thio)quinoline-3-carboxylic acid (600 mg, 2.92 mmol) in DMF (15.0 mL) were added 1-hydroxypyrrolidine-2,5-dione (505 mg, 4.39 mmol), triethyl amine (1.22 mL, 8.77 mmol) and EDCl (1.121 g, 5.85 mmol) at room temperature. After stirring overnight, the reaction mixture was concentrated. The resulting residue was dissolved in H₂O/EA and filtered. The solid was collected (181 mg). The filtrate was separated. The aqueous phase was extracted with EA and the combined organic phase was dried over anhydrous Na₂SO₄, filtered and concentrated. The resulting residue was purified via silica gel column chromatography (dichloromethane/ethyl acetate: 5%~25%) to obtain a mixture which was washed with ethyl acetate to give the desired product (60 mg) as white solid. The combined yield is 41%. $^1$H NMR (400 MHz, DMSO): δ 9.49 (s, 1H), 9.36 (d, J=1.6 Hz, 1H), 8.17 (d, J=6.8 Hz, 1H), 8.00 (d, J=6.0 Hz, 1H), 7.72 (t, J=6.4 Hz, 1H), 2.96 (s, 4H). $^{13}$C NMR (125 MHz, DMSO): δ 170.7, 161.3, 148.8, 147.5, 141.4, 135.1, 129.2, 128.5, 128.3, 127.2, 119.2, 26.1. ESI-MS Calcd for $C_{28}H_{19}N_4O_8S_2$ [M+H]$^+$: 603.06, Found: 603.06.

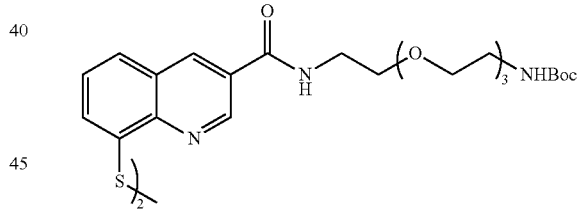

To a solution of the NHS ester (40 mg, 0.132 mmol) in DMF were added Et₃N (0.055 mL, 0.40 mmol) and the amine (51 mg, 0.132 mmol) at room temperature. After stirring for 12 h, the reaction mixture was concentrated. The resulting residue was purified via silica gel column chromatography (dichloromethane/methanol: 5%~15%) to give the desired product (61 mg, 96%) as a white solid. $^1$H NMR (400 MHz, CDCl₃): δ 9.38 (s, 1H), 8.72 (d, J=2.0 Hz, 1H), 7.92 (d, J=7.6 Hz, 1H), 7.72 (d, J=8.0 Hz, 1H), 7.65 (brs, 1H), 7.44 (dd, J=8.0, 7.6 Hz, 1H), 3.80-3.55 (m, 12H), 3.53-3.45 (m, 2H), 3.30-3.18 (m, 2H), 1.37 (s, 9H). $^{13}$C NMR (125 MHz, CDCl₃): δ 172.5, 172.5, 165.8, 156.3, 147.7, 146.5, 136.7, 135.29, 128.0, 127.9, 127.5, 127.4, 126.7, 79.5, 70.5, 70.5, 70.3, 70.2, 69.9, 40.4, 40.3, 28.5. ESI-MS Calcd for $C_{46}H_{65}N_6O_{12}S_2$ [M+H]$^+$: 957.41, Found: 957.25.

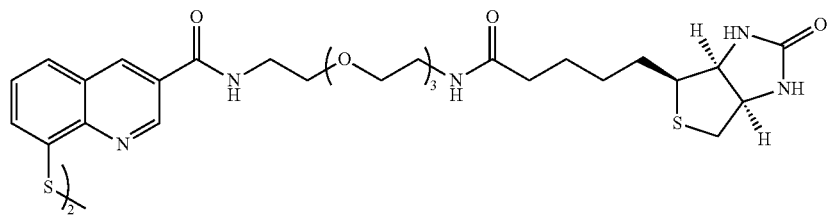

A solution of the Boc protected amine (51 mg, 0.106 mmol) in MeOH (4.0 mL) was added 1 N HCl (1.0 mL) and stirred at 50° C. for 6 h. TLC showed that the SM was completely consumed. The reaction mixture was diluted with MeOH and concentrated. The resulting residue was used in the next step without further purification.

To a solution of the free amine (40 mg, 0.106 mmol) in DMF were added Et$_3$N (0.044 mL, 0.318 mmol) and Biotin NHS ester (36 mg, 0.106 mmol) at room temperature. After stirring for 12 h, the reaction mixture was concentrated. The resulting residue was purified via silica gel column chromatography (dichloromethane/methanol: 10% 25%) to give the desired product (60 mg, 93%) as a white solid. $^1$H NMR (400 MHz, CD$_3$OD/CDCl$_3$ (v/v, 1/2)): δ 9.34 (s, 1H), 8.75 (s, 1H), 7.90 (d, J=7.2 Hz, 1H), 7.75 (d, J=8.0 Hz, 1H), 7.45 (t, J=7.6 Hz, 1H), 4.44-4.36 (m, 1H), 4.24-4.15 (m, 1H), 3.56-3.51 (m, 2H), 3.48-3.42 (m, 2H), 3.33-3.26 (m, 3H), 3.06-2.96 (m, 1H), 2.79 (dd, J=12.8, 4.8 Hz, 1H), 2.63 (d, J=12.8 Hz, 1H), 2.13-2.03 (m, 2H), 1.62-1.43 (m, 2H), 1.35-1.22 (m, 2H). $^{13}$C NMR (125 MHz, CD$_3$OD/CDCl$_3$ (v/v, 1/2)): δ 174.2, 165.8, 164.1, 147.7, 145.9, 137.4, 134.7, 128.1, 128.0, 127.6, 127.1, 70.5, 70.0, 69.9, 69.8, 69.7, 62.0, 60.3, 55.6, 40.4, 40.1, 39.2, 35.7, 28.4, 28.1, 25.5. ESI-MS Calcd for C$_{56}$H$_{77}$N$_{10}$O$_{12}$S$_4$ [M+H]$^+$: 1209.46. Found: 1209.63.

Example 75

Rpn11 Activity Assay. The Rpn11 assay is described in PubChem AID 588493, the entire content of which is incorporated herein by reference. In brief, in order to measure the Rpn11 activity, a synthetic peptide substrate, termed Ub4-pepOG, was engineered. It consists of four linear ubiquitins and a short peptide sequence to which is attached a molecule of the fluorophore Oregon Green 488. The bond between the fourth ubiquitin and the peptide sequence is cleaved by 26S proteasome in vitro, which can be observed by SDS-PAGE and fluorescence polarization measurement. Peptide substrate Ub4-pepOG consists of only 30 amino acids and therefore the decrease of polarization is mainly from deubiquitination but not the proteolysis of the peptide. Fluorescence polarization assay was performed in a low-volume 384 well solid black plate where the components are added in the follow sequence: 1) 5 µl compound in 3% DMSO or 3% DMSO control 2) 5 µl 26S proteasome (Enzo Life Sciences Inc, NY). 5 µl of substrate (15 nM Ub4-pepOG) was added before the measurement to initiate the reaction. Fluorescence polarization is measured using a PHERAstar (BMG labtech, Ortenberg, Germany) plate reader with excitation of 480 nm and emission of 520 nm filter set. To calculate the IC50 of Rpn11 inhibitors, titration was performed for each compound with (8 or 12) different concentration up to 100 µM in quadruplicates. Rpn11 activity was normalized to DMSO control and fitted using does-response curve.

Example 76

Csn5 Activity Assay. The Csn5 assay is described in PubChem AID 651999 the entire content of which is herein incorporated by reference. In brief, a fluorescent substrate termed SCF$^{skp2}$-Nedd8OG was produced to measure CSN5 activity in vitro. This assay measures the decrease in fluorescence polarization due to the decrease in apparent molecular weight of Oregon Green (OG) fluorophore (from the ~175 kDa substrate to ~9 kDa Nedd8OG) as a result of Csn5-mediated cleavage of the isopeptide bond that links Nedd8OG to SCF$^{Skp2}$. The assay was performed in a low-volume 384 well solid black plate comprising equal volumes of compound, substrate (SCF$^{skp2}$-Need8OG) and enzyme (purified COP9 Signalosome Complex, CSN). Fluorescence polarization was recorded using the same setting as for the Rpn11 activity assay. IC$_{50}$ was calculated as described in Example 75.

Example 77

AMSH Activity Assay. AMSH is known to selectively cleave ubiquitin chains in which the ubiquitins are joined via K63 of the proximal ubiquitin linked by an isopeptide bond to the carboxy terminus of the distal ubiquitin. A substrate with this structure, termed DiUb$^{K63}$TAMRA, was purchased from BostonBiochem to assay AMSH activity in vitro as described in Arnst et al., 2013, Anal Biochem, 440; 71-77, the entire content of which is herein incorporated by reference. In brief, DiUb$^{K63}$TAMRA was labeled with quench pairs TAMRA/QXL. Upon AMSH cleavage, TAMRA was separated from the quencher QXL which resulted in an increase of TAMRA fluorescence intensity monitored using Ex540 and Em 590 wavelengths. The titration was performed in a low-volume 384 well solid black plate and analyzed as described in Example 75.

Example 78

Characterization of the Compound Activity in Cells. A reporter degradation assay as described in Chou and Deshaies, 2011, JBC, 286: 16546-16554, the entire content of which is herein incorporated by reference. In brief, stably transfected Hela cells expressing the proteasome substrate Ub$^{G76V}$-GFP were treated with the reversible proteasome inhibitor MG132, which increased the level of Ub$^{G76V}$-GFP to yield a detectable fluorescent signal. After 4 hours, MG132 was removed and a cycloheximide (CHX) chase was initiated +/− different concentrations of test compound and the rate of reporter degradation was evaluated by monitoring GFP fluorescence by high throughput microscopy. The rate of fluorescence decrease was normalized to DMSO control and analyzed using does-response equation.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A compound represented by Formula 1a:

Formula 1a where each of $R_2$, $R_3$, $R_4$, $R_5$, $R_6$, and $R_7$ is independently selected from hydrogen (H), substituted and unsubstituted alkyl groups, carboxyl groups, or substituted and unsubstituted carboxyamido groups;
where at least one of $R_2$, $R_3$, $R_4$, $R_5$, $R_6$, and/or $R_7$ of Formula 1 a is a group represented by Formula 1 b Formula 1b wherein in Formula 1 b:
n is 0, 1, 2, 3, or 4;
* represents a binding site to Formula 1 a;
each of $R_8$ and $R_9$ are independently selected from hydrogen or methyl groups; and
$R_{10}$ is represented by one of Formulae 2, 2a and 4-6 where * in Formulae 2 and 4-6 represents a binding site to Formula 1 b, Formula 2

Formula 3

Formula 4

Formula 5

Formula 6 wherein in Formulae 2, 2a and 4-6:
each of $X_1$, $X_2$, $X_3$, $X_4$, $X_5$, and $X_6$ is independently selected from S, C, N, or O;
$R_{11}$ and $R_{12}$ are each independently selected from:
H,
unsubstituted alkyl groups,
fluorine (F),
trifluoromethyl groups,
carboxyl groups,
CO2CH2CH3 groups,
OCH3 groups,
phenyl groups,
morpholino groups, or
alkyl groups substituted with one or more substituents, at least one of which substituents is selected from the group consisting of amino groups, amido groups, carboxyl groups, and thiol groups;
a is 0 or 1, wherein when a is 1, $X_5$ and $X_6$ form a pi bond; and
$R_{13}$ and $R_{14}$ are each independently selected from H, substituted or unsubstituted alkyl groups, fluorine (F), trifluoromethyl groups, carboxyl groups, CO2CH2CH3 groups, OCH3 groups, phenyl groups, or morpholino groups;
where when $R_{10}$ is represented by Formula 4, $R_3$ is represented by Formula 1 b;
where when $R_{10}$ is represented by Formula 4 and each of $X_3$, $X_4$, $X_5$, and $X_6$ are C, then a is 1 and at least one of $R_{11}$ and $R_{12}$ is fluorine (F), a trifluoromethyl group, a carboxyl group, a CO2CH2CH3 group, a OCH3 group, a phenyl group, or a morpholino group.

2. The compound of claim 1, wherein each of $R_2$, $R_3$, $R_4$, $R_5$, $R_6$, and $R_7$ is independently selected from H, substituted and unsubstituted C1-C12 alkyl groups, carboxyl groups, or substituted and unsubstituted carboxyamido groups.

3. The compound of claim 1, wherein the substituted alkyl groups are selected from the group consisting of alkyl groups having at least one substituent selected from the group consisting of amino groups, amido groups, carboxyl groups, and thiol groups.

4. The compound of claim 1, wherein the substituted carboxyamides are selected from the group consisting of carboxyamides having at least one substituent selected from the group consisting of substituted and unsubstituted C1-C12 alkyl groups, acetyl groups, oxazolyl groups, thiazolyl groups, tetrahydrofuranyl groups, furanyl groups, thiophenyl groups, pyridinyl groups, phenyl groups, fluorophenyl groups, trifluorophenyl groups, methoxyphenyl groups, dioxolylmethylphenyl groups, morphilino groups, and morpholinophenyl groups.

5. The compound of claim 4, wherein the substituted carboxyamides are selected from the group consisting of carboxyamides having at least one substituent selected from the group consisting of substituted C1-C12 alkyl groups is having at least one substituent selected from acetyl groups, oxazolyl groups, thiazolyl groups, tetrahydrofuranyl groups, furanyl groups, thiophenyl groups, pyridinyl groups, phenyl groups, fluorophenyl groups, trifluorophenyl groups, methoxyphenyl groups, dioxolylmethylphenyl groups, morphilino groups, or morpholinophenyl groups.

6. The compound of claim 1, wherein the substituted alkyl groups of $R_{13}$ and $R_{14}$ of Formula 2a have at least one substituent selected from the group consisting of amino groups, amido groups, carboxyl groups, and thiol groups.

7. The compound of claim 1, wherein:
at least one of $R_3$, $R_4$, $R_5$, and/or $R_6$ is represented by Formula 1 b,
each of $R_2$ and $R_7$ is hydrogen (H), and
$R_{10}$ of Formula 1b is represented by Formula 2a.

8. The compound of claim 1, wherein:
at least one of $R_3$ or $R_4$ is represented by Formula 1 b,
each of $R_2$ and $R_7$ is hydrogen (H), and
$R_{10}$ of Formula 1b is represented by Formula 2a.

9. The compound of claim 1, wherein:
at least one of $R_5$ or $R_6$ is represented by Formula 1 b,
each of $R_2$ and $R_7$ is hydrogen (H), and
$R_{10}$ of Formula 1b is represented by Formula 2a.

10. A compound represented by one of Compounds 5, 8, 9, 11, 12, 15, 17, 18, 19, 20, 21, 24, 27, 28, 31, or 32:

-continued

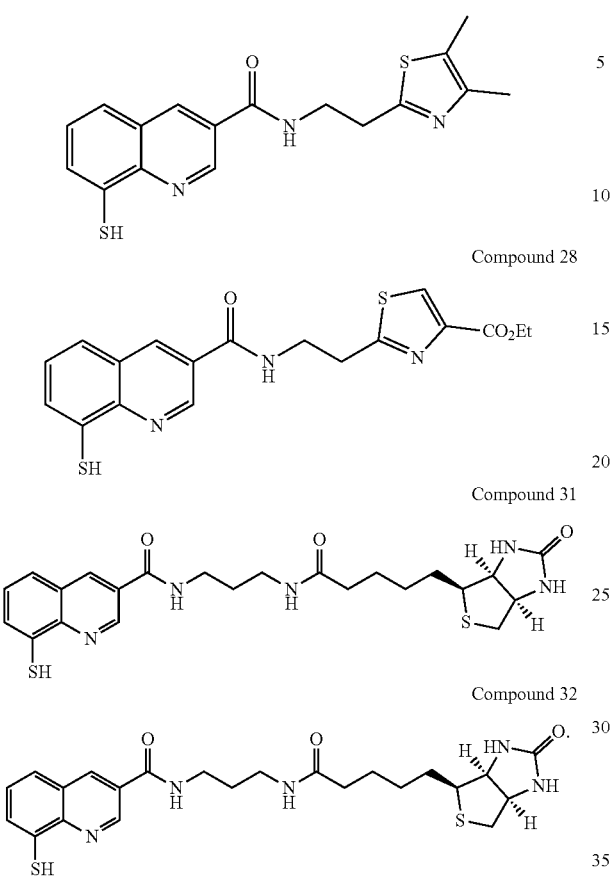

11. A compound represented by Formula 1a:

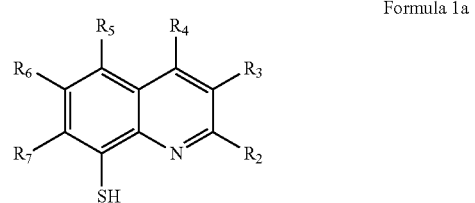

where each of $R_2$, $R_3$, $R_4$, $R_5$, $R_6$, and $R_7$ is independently selected from hydrogen (H), substituted and unsubstituted alkyl groups, carboxyl groups, or substituted and unsubstituted carboxyamido groups;

where at least one of $R_2$, $R_3$, $R_4$, $R_5$, $R_6$, and/or $R_7$ of Formula 1 a is a group represented by Formula 1 b

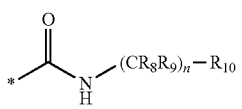

wherein in Formula 1 b:
n is 0, 1, 2, 3, or 4;
*represents a binding site to Formula 1 a;
each of $R_8$ and $R_9$ are independently selected from hydrogen or methyl groups; and
$R_{10}$ is represented by one of Formulae 2, 2a, 5, or 6 where * in Formulae 2, 2a, 5, and 6 represents a binding site to Formula 1 b,

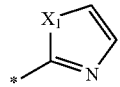

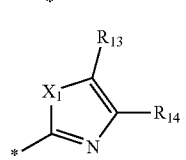

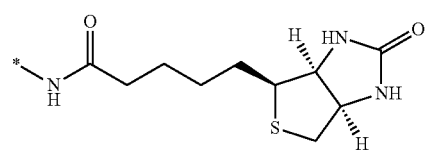

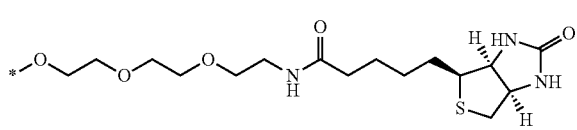

wherein in Formulae 2, 2a, and 6:
$X_1$, is independently selected from S, C, N, or O;
$R_{13}$ and $R_{14}$ are each independently selected from:
H,
unsubstituted alkyl groups,
fluorine (F),
trifluoromethyl groups,
carboxyl groups,
CO2CH2CH3 groups,
OCH3 groups,
phenyl groups,
morpholino groups, and
alkyl groups substituted with one or more substituents, at least one of which substituents is selected from the group consisting of amino groups, amido groups, carboxyl groups, and thiol groups.

12. A method of inhibiting Rpn11 in a cell, a cell culture, or a cell in a human or animal subject, comprising:
administering the compound of claim 1 to the cell, the cell culture, or to the cell in the human or animal subject.

13. A method of inhibiting Rpn11 in a cell, a cell culture, or a cell in a human or animal subject, the method comprising:
administering the compound of claim 10 to the cell, the cell culture, or to the cell in the human or animal subject.

14. The compound of claim 11, wherein:
at least one of $R_3$ or $R_4$ is represented by Formula 1 b,
each of $R_2$ and $R_7$ is hydrogen (H), and
$R_{10}$ of Formula 1b is represented by Formula 2a.

15. The compound of claim 11, wherein:
at least one of $R_5$ or $R_6$ is represented by Formula 1 b,
each of $R_2$ and $R_7$ is hydrogen (H), and
$R_{10}$ of Formula 1b is represented by Formula 2a.

16. The compound of claim 11, wherein each of $R_2$, $R_3$, $R_4$, $R_5$, $R_6$, and $R_7$ is independently selected from H, substituted and unsubstituted C1-C12 alkyl groups, carboxyl groups, or substituted and unsubstituted carboxyamido groups.

17. The compound of claim 11, wherein the substituted alkyl groups are selected from the group consisting of alkyl groups substituted with one or more substituents, at least one of which substituents is selected from the group consisting of amino groups, amido groups, carboxyl groups, and thiol groups.

18. The compound of claim 11, wherein the substituted carboxyamido groups are selected from the group consisting of carboxyamido groups substituted with one or more substituents, at least one of which substituents is selected from the group consisting of substituted and unsubstituted C1-C12 alkyl groups, acetyl groups, oxazolyl groups, thiazolyl groups, tetrahydrofuranyl groups, furanyl groups, thiophenyl groups, pyridinyl groups, phenyl groups, fluorophenyl groups, trifluorophenyl groups, methoxyphenyl groups, dioxolylmethylphenyl groups, morphilino groups, and morpholinophenyl groups.

* * * * *